United States Patent
Harding et al.

(10) Patent No.: US 9,279,016 B2
(45) Date of Patent: Mar. 8, 2016

(54) METHODS FOR IDENTIFYING ANTIBODIES WITH REDUCED IMMUNOGENICITY

(71) Applicant: AbbVie Biotherapeutics Inc., Redwood City, CA (US)

(72) Inventors: Fiona A. Harding, Mountain View, CA (US); Olivia Jennifer Razo, Newark, CA (US)

(73) Assignee: AbbVie Biotherapeutics Inc., Redwood City, CA (US)

( * ) Notice: Subject to any disclaimer, the term of this patent is extended or adjusted under 35 U.S.C. 154(b) by 207 days.

(21) Appl. No.: 14/030,977

(22) Filed: Sep. 18, 2013

(65) Prior Publication Data

US 2014/0227251 A1 Aug. 14, 2014

Related U.S. Application Data

(60) Provisional application No. 61/703,170, filed on Sep. 19, 2012.

(51) Int. Cl.
*C40B 40/10* (2006.01)
*C07K 16/24* (2006.01)
*G01N 33/68* (2006.01)
*C07K 16/42* (2006.01)
*A61K 39/00* (2006.01)

(52) U.S. Cl.
CPC ........... *C07K 16/241* (2013.01); *C07K 16/4208* (2013.01); *G01N 33/6854* (2013.01); *A61K 2039/505* (2013.01); *C40B 40/10* (2013.01); *G01N 2333/525* (2013.01); *G01N 2500/10* (2013.01)

(58) Field of Classification Search
None
See application file for complete search history.

(56) References Cited

U.S. PATENT DOCUMENTS 6,090,382 A 7/2000 Salfeld et al.

FOREIGN PATENT DOCUMENTS

WO WO 2009/032128 A1 3/2009

OTHER PUBLICATIONS

Gonzales et al., 2005 "Minimizing the Immunogenicity of Antibodies for Clinical Application," *Tumor Biology*, 26(1):31-43.
Harding et al., 2010 "The immunogenicity of humanized and fully human antibodies: Residual immunogenicity resides in the CDR regions," *Landes Bioscience*, 2(3):256-265.
Léger et al., 2012 "Humanization of Antibodies," Retrieved from the Internet: URL:http://www.icpress.co.uk/etextbook/p743/p743_chap01.pdf [retrieved on Jul. 12, 2012].
Yoon et at , 2006 "Construction, Affinity Mautration, and Biological Characterization of an Anti-tumor-associated Glycoprotein-72 Humanized Antibody,"*J. Biol. Chem.*, 281(11):6985-6992.
International Search Report and Written Opinion mailed Sep. 25, 2014 corresponding to related International Patent Application No. PCT/US2013/060480.

*Primary Examiner* — Christian Boesen
(74) *Attorney, Agent, or Firm* — Dechert LLP

(57) ABSTRACT

The disclosure describes methods of identifying a variant of a reference antibody with reduced immunogenicity as compared to the reference antibody. The disclosure further describes variants of a reference anti-TNF-α antibody having reduced immunogenicity as compared to the reference anti-TNF-α reference antibody.

12 Claims, 25 Drawing Sheets

| Antibody Chain | CDR No. | Sequence | SEQ ID NO. |
|---|---|---|---|
| Heavy | 1 | DYAMH | 5 |
| Heavy | 2 | AITWNSGHIDYADSVEG | 6 |
| Heavy | 3 | VSYLSTASSLDY | 7 |
| Light | 1 | RASQGIRNYLA | 8 |
| Light | 2 | AASTLQS | 9 |
| Light | 3 | QRYNRAPYT | 10 |

D2E7(Adalimumab, HUMIRA) V_H (SEQ ID NO:2)

EVQLVESGGGLVQPGRSLRLSCAASGFTFDDYAMHWVRQAPGKGLEWVSAITWNSGHIDYADSVEGR
FTISRDNAKNSLYLQMNSLRAEDTAVYYCAKVSYLSTASSLDYWGQGTLVTVSS

D2E7 (Adalimumab, HUMIRA) V_L (SEQ ID NO:4)

DIQMTQSPSSLSASVGDRVTITCRASQGIRNYLAWYQQKPGKAPKLLIYAASTLQSGVPSRFSGSGSGT
DFTLTISSLQPEDVATYYCQRYNRAPYTFGQGTKVEIK

FIG. 1A

| Antibody Chain | CDR No. | Sequence | SEQ ID NO. |
|---|---|---|---|
| Heavy | 1 | DYAMH | 5 |
| Heavy | 2 | AITWNSGHIDYADSVEG | 6 |
| Heavy | 3 | VSYLSTASSLDY | 7 |
| Light | 1 | RASQGIRNYLA | 8 |
| Light | 2 | AASTLQS | 9 |
| Light | 3 | QRYNRAPYT | 10 |

FIG. 1B

| | |
|---|---|
| GAGGTGCAGC TGGTGGAGTC TGGGGGAGGC TTGGTACAGC CCGGCAGGTC CCTGAGACTC | 60 |
| TCCTGTGCGG CCTCTGGATT CACCTTTGAT GATTATGCCA TGCACTGGGT CCGGCAAGCT | 120 |
| CCAGGGAAGG GCCTGGAATG GGTCTCAGCT ATCACTTGGA ATAGTGGTCA CATAGACTAT | 180 |
| GCGGACTCTG TGGAGGGCCG ATTCACCATC TCCAGAGACA ACGCCAAGAA CTCCCTGTAT | 240 |
| CTGCAAATGA ACAGTCTGAG AGCTGAGGAT ACGGCCGTAT ATTACTGTGC GAAAGTCTCG | 300 |
| TACCTTAGCA CCGCGTCCTC CCTTGACTAT TGGGGCCAAG GTACCCTGGT CACCGTCTCG | 360 |
| AGT | 363 |

Nucleotide Sequence of D2E7 Variable Heavy Chain

| | |
|---|---|
| GACATCCAGA TGACCCAGTC TCCATCCTCC CTGTCTGCAT CTGTAGGGGA CAGAGTCACC | 60 |
| ATCACTTGTC GGGCAAGTCA GGGCATCAGA AATTACTTAG CCTGGTATCA GCAAAAACCA | 120 |
| GGGAAAGCCC CTAAGCTCCT GATCTATGCT GCATCCACTT TGCAATCAGG GGTCCCATCT | 180 |
| CGGTTCAGTG GCAGTGGATC TGGGACAGAT TTCACTCTCA CCATCAGCAG CCTACAGCCT | 240 |
| GAAGATGTTG CAACTTATTA CTGTCAAAGG TATAACCGTG CACCGTATAC TTTTGGCCAG | 300 |
| GGGACCAAGG TGGAAATCAA A | 321 |

Nucleotide Sequence of D2E7 Variable Light Chain

FIG. 1C

| position | kabat | WT amino acid | beneficial mutations in $V_L$ |
|---|---|---|---|
| L1-1 | 24 | R | |
| L1-2 | 25 | A | |
| L1-3 | 26 | S | |
| L1-4 | 27 | Q | |
| L1-5 | 28 | G | $F^{ab}, I^{ab}, V^{b}, W^{bc}, Y^{ab}$ |
| L1-6 | 29 | I | |
| L1-7 | 30 | R | $I^{ab}, T^{abc}, V^{abc}$ |
| L1-8 | 31 | N | $A^{abc}, D^{ac}, E^{ac}, G^{abc}, L^{abc}, M^{abc}, Q^{abc}, R^{abc}, T^{abc}$ |
| L1-9 | 32 | Y | |
| L1-10 | 33 | L | |
| L1-11 | 34 | A | |
| | | | |
| L2-1 | 50 | A | $I^{bc}, T^{bc}, V^{abc}$ |
| L2-2 | 51 | A | |
| L2-3 | 52 | S | |
| L2-4 | 53 | T | $D^{bc}$ |
| L2-5 | 54 | L | |
| L2-6 | 55 | Q | |
| L2-7 | 56 | S | |
| | | | |
| L3-1 | 89 | Q | |
| L3-2 | 90 | R | $G^{a}$ |
| L3-3 | 91 | Y | |
| L3-4 | 92 | N | $F^{abc}, M^{ab}, W^{abc}, Y^{c}$ |
| L3-5 | 93 | R | $L^{a}, N^{a}, W^{ab}, Y^{a}$ |
| L3-6 | 94 | A | |
| L3-7 | 95 | P | |
| L3-8 | 96 | Y | |
| L3-9 | 97 | T | $Y^{c}$ |

FIG. 2

| position | kabat | WT amino acid | beneficial mutations in $V_H$ |
|---|---|---|---|
| H1-1 | 31 | D | $S^d$ |
| H1-2 | 32 | Y | $A^d, C^d, K^d, M^d, R^d, S^d, V^d$ |
| H1-3 | 33 | A | |
| H1-4 | 34 | M | |
| H1-5 | 35 | H | $C^d, D^d, E^d, S^d, T^d$ |
| H2-1 | 50 | A | |
| H2-2 | 51 | I | |
| H2-3 | 52 | T | $A^d, G^d, N^d$ |
| H2-4 | 52a | W | $A^d, F^d, H^d, L^d, M^d, V^d$ |
| H2-5 | 53 | N | $G^e$ |
| H2-6 | 54 | S | $D^e, L^e$ |
| H2-7 | 55 | G | |
| H2-8 | 56 | H | |
| H2-9 | 57 | I | $K^{ef}$ |
| H2-10 | 58 | D | $L^d$ |
| H2-11 | 59 | Y | $A^{ef}, C^{ef}, E^{ef}, F^{ef}, G^{ef}, H^{ef}, I^{ef}, K^{ef}, L^{ef}, M^e, N^{ef}, Q^e, R^{ef}, S^{ef}, V^{ef}, W^{ef},$ |
| H2-12 | 60 | A | $Y^e$ |
| H2-13 | 61 | D | $N^f$ |
| H2-14 | 62 | S | |
| H2-15 | 63 | V | $D^{ef}, L^{ef}, M^{ef}, Q^{ef}, T^{ef}$ |
| H2-16 | 64 | E | $F^{ef}, H^e, K^{ef}, R^{ef}, T^{ef}, W^{ef}$ |
| H2-17 | 65 | G | $A^{ef}, C^{ef}, E^{ef}, H^e, I^{ef}, K^{ef}, L^{ef}, M^{ef}, N^{ef}, P^{ef}, Q^{ef}, R^{ef}, S^{ef}, T^{ef}, Y^{ef}$ |

FIG. 3A

| position | kabat | WT amino acid | beneficial mutations in $V_H$ |
|---|---|---|---|
| H3-1 | 95 | V | $G^d, R^d, W^d$ |
| H3-2 | 96 | S | |
| H3-3 | 97 | Y | |
| H3-4 | 98 | L | $T^d, V^d$ |
| H3-5 | 99 | S | |
| H3-6 | 100 | T | $V^d$ |
| H3-7 | 100a | A | |
| H3-8 | 100b | S | |
| H3-9 | 100c | S | $K^d, W^e, Y^e$ |
| H3-10 | 100d | L | |
| H3-11 | 101 | D | $V^d$ |
| H3-12 | 102 | Y | |

FIG. 3B

| WT-AA | WT | AA | Mutant | CDR | position | | 1H11 ER | TNF-α-ER |
|---|---|---|---|---|---|---|---|---|
| D | GAC | D | GAT | CDR-H1 | 1 | | 0.29 | 1.47 |
| A | GCC | A | GCG | CDR-H1 | 3 | | 0.06 | 1.64 |
| A | GCC | A | GCT | CDR-H1 | 3 | | 0.4 | 1.33 |
| H | CAC | H | CAT | CDR-H1 | 5 | | 0.14 | 1.46 |
| A | GCG | A | GCT | CDR-H2 | 1 | | 0.3 | 1.08 |
| I | ATC | I | ATT | CDR-H2 | 2 | | 0.08 | 1.23 |
| T | ACG | T | ACT | CDR-H2 | 3 | | 0.44 | 1.36 |
| N | AAC | N | AAT | CDR-H2 | 5 | | 0.27 | 1.63 |
| G | GGC | G | GGG | CDR-H2 | 7 | | 0.16 | 1.46 |
| G | GGC | G | GGT | CDR-H2 | 7 | | 0.07 | 1.27 |
| H | CAC | H | CAT | CDR-H2 | 8 | | 0.19 | 1.38 |
| I | ATA | I | ATT | CDR-H2 | 9 | | 0.01 | 1.85 |
| A | GCA | A | GCT | CDR-H2 | 12 | | 0.02 | 1.47 |
| A | GCA | A | GCG | CDR-H2 | 12 | | 0.02 | 1.11 |
| S | AGC | S | TCT | CDR-H2 | 14 | | 0.01 | 1.57 |
| S | AGC | S | TCG | CDR-H2 | 14 | | 0 | 1.58 |
| S | AGC | S | AGT | CDR-H2 | 14 | | 0.07 | 1.14 |
| V | GTG | V | GTT | CDR-H2 | 15 | | 0.04 | 1.52 |
| E | GAA | E | GAG | CDR-H2 | 16 | | 0.13 | 1.72 |
| G | GGA | G | GGT | CDR-H2 | 17 | | 0.02 | 1.29 |
| G | GGA | G | GGG | CDR-H2 | 17 | | 0.02 | 1.44 |
| S | AGC | S | AGT | CDR-H3 | 2 | | 0.12 | 1.27 |
| L | CTC | L | CTT | CDR-H3 | 4 | | 0.07 | 1.43 |
| L | CTC | L | TTG | CDR-H3 | 4 | | 0.02 | 1.43 |
| L | CTC | L | CTG | CDR-H3 | 4 | | 0.02 | 1.50 |
| S | TCA | S | TCG | CDR-H3 | 5 | | 0.2 | 1.45 |
| S | TCA | S | TCT | CDR-H3 | 5 | | 0.01 | 1.40 |
| S | TCA | S | AGT | CDR-H3 | 5 | | 0.04 | 1.39 |
| T | ACA | T | ACT | CDR-H3 | 6 | | 0.08 | 1.14 |
| A | GCT | A | GCG | CDR-H3 | 7 | | 0.27 | 1.22 |
| S | TCC | S | AGT | CDR-H3 | 8 | | 0 | 1.53 |
| S | TCC | S | TCG | CDR-H3 | 8 | | 0.02 | 1.53 |
| S | TCC | S | TCT | CDR-H3 | 8 | | 0.46 | 0.92 |
| S | AGC | S | TCG | CDR-H3 | 9 | | 0 | 1.63 |
| S | AGC | S | AGT | CDR-H3 | 9 | | 0.14 | 1.19 |
| L | CTA | L | TTG | CDR-H3 | 10 | | 0 | 1.34 |
| Y | TAC | Y | TAT | CDR-H3 | 12 | | 0.34 | 1.34 |

| | 1H11 | TNF-α | Neutral binding to TNF-α |
|---|---|---|---|
| average | 0.12 | 1.40 | 1.21-1.59 |
| SD | 0.13 | 0.19 | |

FIG. 9

|   | 1 | 2 | 3 | 4 | 5 | 6 | 7 | 8 |
|---|---|---|---|---|---|---|---|---|
| A | VL CDR1-1 R24 | VL CDR1-9 Y32 | VL CDR2-6 Q55 | VL CDR3-7 P95 | VH CDR2-1 A50 | VH CDR2-9 I57 | VH CDR2-17 G65 | VH CDR3-8 S100b |
| B | VL CDR1-2 A25 | VL CDR1-10 L33 | VL CDR2-7 S56 | VL CDR3-8 Y96 | VH CDR2-2 I51 | VH CDR2-10 D58 | VH CDR3-1 V95 | VH CDR3-9 S100c |
| C | VL CDR1-3 S26 | VL CDR1-11 A34 | VL CDR3-1 Q89 | VL CDR3-9 T97 | VH CDR2-3 T52 | VH CDR2-11 Y59 | VH CDR3-2 S96 | VH CDR3-10 L100d |
| D | VL CDR1-4 Q27 | VL CDR2-1 A50 | VL CDR3-2 R90 | VH CDR1-1 D31 | VH CDR2-4 W52a | VH CDR2-12 A60 | VH CDR3-3 Y97 | VH CDR3-11 D101 |
| E | VL CDR1-5 G28 | VL CDR2-2 A51 | VL CDR3-3 Y91 | VH CDR1-2 Y32 | VH CDR2-5 N53 | VH CDR2-13 D61 | VH CDR3-4 L98 | VH CDR3-12 Y102 |
| F | VL CDR1-6 I29 | VL CDR2-3 S52 | VL CDR3-4 N92 | VH CDR1-3 A33 | VH CDR2-6 S54 | VH CDR2-14 S62 | VH CDR3-5 S99 | |
| G | VL CDR1-7 R30 | VL CDR2-4 T53 | VL CDR3-5 R93 | VH CDR1-4 M34 | VH CDR2-7 G55 | VH CDR2-15 V63 | VH CDR3-6 T100 | |
| H | VL CDR1-8 N31 | VL CDR2-5 L54 | VL CDR3-6 A94 | VH CDR1-5 H35 | VH CDR2-8 H56 | VH CDR2-16 E64 | VH CDR3-7 A100a | |

FIG. 10

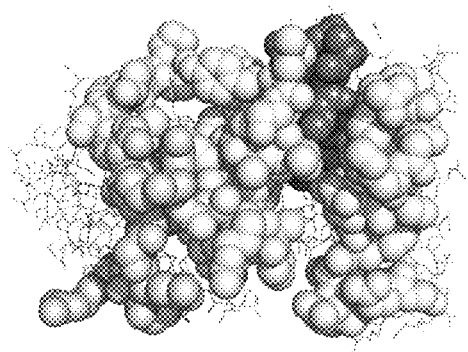
A
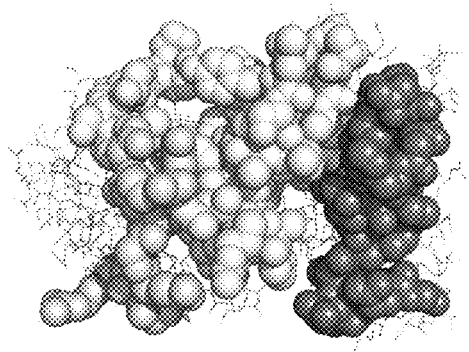
B
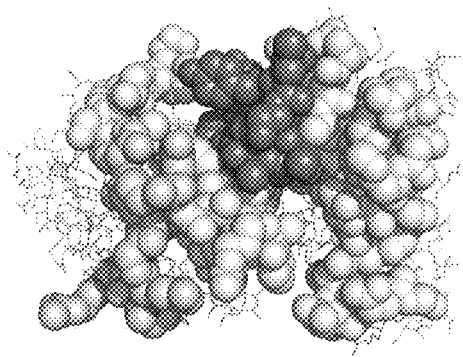
C
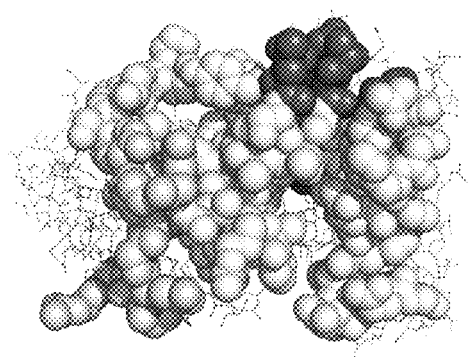
D
FIG. 13A-D

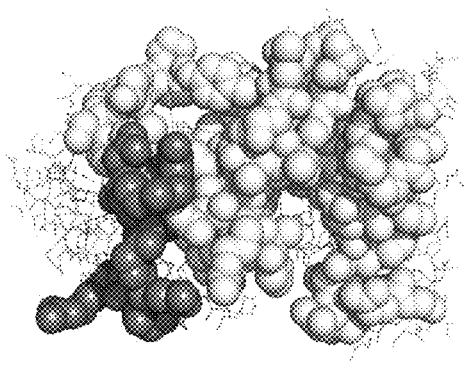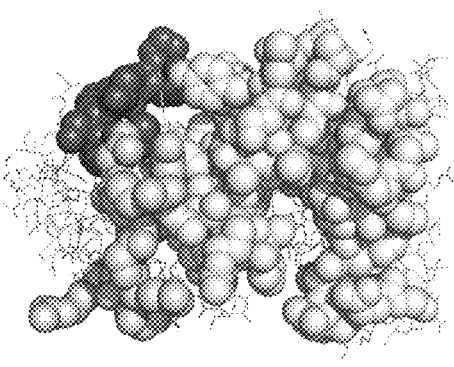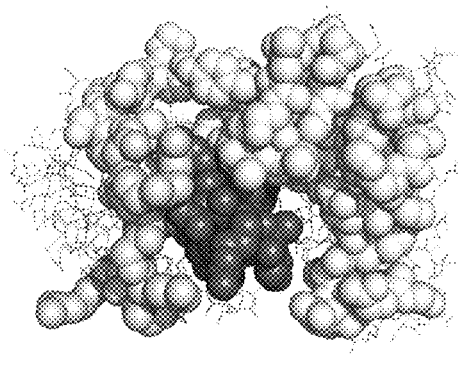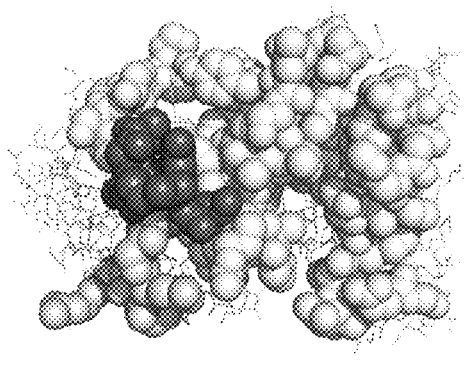
FIG. 14A-D

| AA | CDR | position | 1H11 ER | Avg 1H11 ER in position | TNFα-ER |
|---|---|---|---|---|---|
| A | CDR-H1 | 2 | 5.22 | 5.69 | 1.37 |
| A | CDR-H1 | 2 | 6.21 | 5.69 | 1.32 |
| C | CDR-H1 | 2 | 11.17 | 5.69 | 1.22 |
| D | CDR-H1 | 2 | 0.56 | 5.69 | 0.03 |
| E | CDR-H1 | 2 | 0.44 | 5.69 | 0.00 |
| F | CDR-H1 | 2 | 0.03 | 5.69 | 1.32 |
| G | CDR-H1 | 2 | 6.95 | 5.69 | 0.39 |
| G | CDR-H1 | 2 | 5.42 | 5.69 | 0.25 |
| H | CDR-H1 | 2 | 3.58 | 5.69 | 1.14 |
| I | CDR-H1 | 2 | 6.80 | 5.69 | 1.20 |
| K | CDR-H1 | 2 | 9.58 | 5.69 | 1.47 |
| L | CDR-H1 | 2 | 1.44 | 5.69 | 0.95 |
| L | CDR-H1 | 2 | 1.40 | 5.69 | 0.91 |
| L | CDR-H1 | 2 | 1.29 | 5.69 | 0.64 |
| M | CDR-H1 | 2 | 4.37 | 5.69 | 1.25 |
| N | CDR-H1 | 2 | 8.40 | 5.69 | 1.60 |
| P | CDR-H1 | 2 | 1.22 | 5.69 | 0.38 |
| P | CDR-H1 | 2 | 1.03 | 5.69 | 0.33 |
| Q | CDR-H1 | 2 | 9.41 | 5.69 | 1.18 |
| R | CDR-H1 | 2 | 8.02 | 5.69 | 1.65 |
| R | CDR-H1 | 2 | 6.88 | 5.69 | 1.46 |
| R | CDR-H1 | 2 | 10.28 | 5.69 | 1.45 |
| S | CDR-H1 | 2 | 7.32 | 5.69 | 1.65 |
| S | CDR-H1 | 2 | 9.20 | 5.69 | 1.44 |
| S | CDR-H1 | 2 | 6.28 | 5.69 | 1.28 |
| T | CDR-H1 | 2 | 9.51 | 5.69 | 1.2 |
| T | CDR-H1 | 2 | 6.48 | 5.69 | 1.14 |
| V | CDR-H1 | 2 | 9.34 | 5.69 | 1.41 |
| V | CDR-H1 | 2 | 6.44 | 5.69 | 1.28 |
| W | CDR-H1 | 2 | 6.50 | 5.69 | 1.19 |

WT binding to TNFα: 1.21 – 1.60
WT binding to 1H11: 0.00 – 0.25

FIG. 16

| Variant | Notation | 37440 | 23709 | 90814 | 84111 | Average | SD |
|---|---|---|---|---|---|---|---|
| WT | WT | 1.67 | -1.16 | 0.00 | -0.44 | 0.02 | 1.20 |
| VL-SS | VL-SS | -2.90 | 3.79 | 0.35 | -0.33 | 0.23 | 2.76 |
| VL R30T | VL4 | 8.44 | 26.36 | 18.92 | 11.19 | 16.23 | 8.08 |
| VH Y59I + VL-SS | VH16-SS | 0.13 | 1.60 | -0.66 | -0.46 | 0.15 | 1.02 |
| VH Y59R + VL-SS | VH20-SS | -1.23 | 2.82 | -1.08 | 1.24 | 0.44 | 1.95 |
| VH V63D + VL-SS | VH24-SS | -0.77 | -0.37 | -0.69 | -0.54 | -0.59 | 0.18 |
| VL G28F | VL1 | 3.15 | 15.50 | 0.69 | 0.22 | 4.89 | 7.19 |
| VL G28V | VL2 | -5.29 | 10.13 | -0.71 | -0.07 | 1.01 | 6.51 |
| VL G28Y | VL3 | -1.46 | 8.33 | -0.16 | 0.00 | 1.68 | 4.48 |
| VL N31D | VL5 | -0.46 | 13.13 | 0.56 | 1.32 | 3.64 | 6.37 |
| VL N31L | VL6 | 3.77 | 10.88 | 1.19 | 1.68 | 4.38 | 4.48 |
| VL N31T | VL7 | 3.43 | 8.70 | 1.04 | 0.88 | 3.51 | 3.65 |
| VL A50T | VL9 | 1.77 | 15.45 | 0.01 | -0.19 | 4.26 | 7.51 |
| VL T53D | VL10 | 0.00 | 3.77 | -1.25 | -0.50 | 0.51 | 2.24 |
| VL N92F | VL11 | 5.96 | 24.50 | 4.50 | 4.41 | 9.85 | 9.80 |
| VL N92Y | VL12 | 7.62 | 22.66 | 6.17 | 6.19 | 10.66 | 8.03 |
| VL R93L | VL13 | 2.14 | 17.92 | 1.19 | 1.92 | 5.79 | 8.09 |
| VL R93N | VL14 | 1.79 | 15.93 | 1.22 | 1.48 | 5.10 | 7.22 |
| VH D31S + VL-SS | VH1-SS | 3.20 | 25.37 | 2.20 | 1.63 | 8.10 | 11.53 |
| VH Y32A + VL-SS | VH2-SS | 8.88 | 31.91 | 4.01 | 2.69 | 11.87 | 13.62 |
| VH Y32R + VL-SS | VH3-SS | 11.81 | 52.68 | 5.85 | 3.80 | 18.54 | 23.02 |
| VH Y32S + VL-SS | VH4-SS | 7.34 | 25.95 | 4.08 | 2.21 | 9.90 | 10.91 |
| VH H35E + VL-SS | VH6-SS | 0.99 | 20.58 | 0.07 | 0.23 | 5.47 | 10.08 |
| VH H35T + VL-SS | VH7-SS | 14.67 | 33.27 | 2.20 | 10.15 | 15.07 | 13.18 |
| VH T52A + VL-SS | VH8-SS | -1.98 | 18.61 | 0.64 | 0.86 | 4.53 | 9.48 |
| VH T52G + VL-SS | VH9-SS | 2.32 | 24.96 | 1.61 | 1.36 | 7.56 | 11.60 |
| VH I57K + VL-SS | VH10-SS | -2.69 | 8.43 | -1.23 | -0.42 | 1.02 | 5.03 |
| VH Y59A + VL-SS | VH12-SS | -2.32 | 4.80 | -1.31 | -1.09 | 0.02 | 3.23 |
| VH Y59C + VL-SS | VH13-SS | -4.39 | 4.37 | -1.01 | -0.49 | -0.38 | 3.61 |
| VH Y59F + VL-SS | VH14-SS | -1.51 | 7.70 | -0.01 | -0.23 | 1.49 | 4.19 |
| VH Y59H + VL-SS | VH15-SS | -0.38 | 6.28 | -0.49 | -0.04 | 1.34 | 3.30 |
| VH Y59L + VL-SS | VH18-SS | -0.74 | 5.37 | -1.39 | -0.48 | 0.69 | 3.14 |
| VH Y59M + VL-SS | VH19-SS | 0.58 | 2.92 | -1.25 | -0.53 | 0.43 | 1.82 |
| VH Y59S + VL-SS | VH21-SS | -2.89 | 6.58 | -1.41 | -1.08 | 0.30 | 4.26 |
| VH Y59V + VL-SS | VH22-SS | -1.52 | 4.05 | -1.24 | 0.20 | 0.37 | 2.56 |
| VH Y59W + VL-SS | VH23-SS | -1.16 | 8.76 | 1.03 | -0.24 | 2.10 | 4.53 |
| VH V63L + VL-SS | VH25-SS | -0.41 | 7.11 | -0.45 | -0.10 | 1.54 | 3.72 |
| VH G65A + VL-SS | VH26-SS | -2.74 | 6.44 | -1.32 | -0.31 | 0.52 | 4.07 |
| VH G65E + VL-SS | VH27-SS | -2.55 | 8.87 | -0.38 | -0.46 | 1.37 | 5.10 |
| VH G65L + VL-SS | VH28-SS | -2.94 | 1.80 | -1.25 | -1.10 | -0.88 | 1.97 |
| VH G65M + VL-SS | VH29-SS | -2.30 | 3.73 | -0.30 | -1.12 | 0.00 | 2.62 |
| VH G65Q + VL-SS | VH30-SS | -1.54 | 5.57 | 1.01 | -0.46 | 1.14 | 3.13 |
| VH G65R + VL-SS | VH31-SS | 3.27 | 7.88 | -0.47 | -0.14 | 2.63 | 3.88 |

Fig. 20A

| Variant | Notation | 37440 | 23709 | 90814 | 84111 | Average | SD |
|---|---|---|---|---|---|---|---|
| VH G65S + VL-SS | VH32-SS | -1.77 | 5.59 | -1.30 | -0.46 | 0.51 | 3.43 |
| VH V95R + VL-SS | VH33-SS | -1.47 | 9.95 | -0.32 | 0.35 | 2.13 | 5.27 |
| VH V95W + VL-SS | VH34-SS | 26.86 | 59.72 | 63.70 | 37.73 | 47.00 | 17.63 |
| VH L98T + VL-SS | VH35-SS | 22.01 | 43.07 | 13.08 | 8.65 | 21.70 | 15.29 |
| VH L98V + VL-SS | VH36-SS | 9.75 | 45.57 | 6.23 | 3.32 | 16.22 | 19.75 |
| VH T100V + VL-SS | VH37-SS | 47.11 | 61.75 | 60.87 | 42.04 | 52.94 | 9.89 |
| VH D101V + VL-SS | VH38-SS | 0.93 | 13.57 | -0.32 | 0.55 | 3.68 | 6.61 |
| VH Y32K + VL-SS | VH39-SS | 13.28 | 35.32 | 6.92 | 4.34 | 14.97 | 14.08 |
| VH Y32V + VL-SS | VH40-SS | 7.07 | 19.62 | 2.17 | 1.36 | 7.56 | 8.43 |
| VH H35C + VL-SS | VH41-SS | 2.04 | 24.36 | 0.94 | 0.77 | 7.03 | 11.57 |
| VH H35S + VL-SS | VH42-SS | 3.09 | 30.19 | 4.08 | 1.16 | 9.63 | 13.76 |
| VH V95G + VL-SS | VH43-SS | 29.10 | 53.62 | 18.01 | 13.00 | 28.43 | 18.09 |
| G28I | | 5.05 | 15.84 | | -0.10 | 6.93 | 8.14 |
| G28W | | 3.54 | 14.89 | | -0.05 | 6.13 | 7.80 |
| R30I | | 18.99 | 44.28 | | 8.46 | 23.91 | 18.41 |
| R30V | | 19.04 | 40.09 | | 10.16 | 23.10 | 15.37 |
| N31E | | 10.69 | 29.20 | | 3.37 | 14.42 | 13.31 |
| N31G | | 6.16 | 19.35 | | 1.03 | 8.85 | 9.45 |
| V31R | | 5.80 | 13.38 | | 0.78 | 6.65 | 6.35 |
| A50V | | 2.15 | 15.98 | | -0.01 | 6.04 | 8.68 |
| R93W | | 6.25 | 28.88 | | 2.34 | 12.49 | 14.33 |
| VH-Y32K | | 36.31 | 24.20 | | | 30.26 | 8.56 |
| VH-Y32V | | 21.20 | 13.50 | | | 17.35 | 5.44 |
| VH-H35C | | 12.70 | 19.40 | | | 16.05 | 4.74 |
| VH-H35S | | 13.99 | 22.56 | | | 18.28 | 6.06 |
| VH-V95G | | 34.70 | 38.58 | | | 36.64 | 2.75 |
| DP10 | | 99.82 | 84.18 | 95.33 | 71.54 | 87.72 | 12.63 |

Fig. 20B

| VH | VL | ADAb bridging | fold affinity | affinity pM |
|---|---|---|---|---|
| WT | WT | 5 | 100 | 83 +/- 10 |
| WT | SS | 0.4 | 82 | 150 |
| Y32K/T100V | SS | 28 | 142 | 61 |
| Y32K/V95G/T100V | SS | 24 | 122 | 71 |
| Y32K | SS/R30T | 45 | 55 | 130 |
| Y32K | SS/R30I | 48 | 50 | 149 |
| V95G/T100V | SS | 15 | 25 | 335 |
| Y32M | SS | 0 | 21 | 411 |
| V95W | R30I | 95 | 23 | 379 |
| V95W | R30T | 97 | 0 | >10,000 |

METHODS FOR IDENTIFYING ANTIBODIES WITH REDUCED IMMUNOGENICITY

1. CROSS REFERENCE TO RELATED APPLICATIONS

This application claims priority under 35 U.S.C. §119(e) claims priority to provisional application Ser. No. 61/703,170, filed Sep. 19, 2012, the contents of which are incorporated by reference herein in their entirety.

2. SEQUENCE LISTING

The instant application contains a Sequence Listing which has been submitted in ASCII format via EFS-Web and is hereby incorporated by reference in its entirety. Said ASCII copy, created on Sep. 17, 2013, is named 381493-721US (118133)_SL.txt and is 6,648 bytes in size.

3. BACKGROUND

B-cell epitopes are the sites of molecules that are recognized by antibodies of the immune system. Identification of B-cell epitopes in therapeutic proteins can be useful in designing variants that do not elicit an immune response when adminstered to patients.

B-cell epitopes can be identified by individually mutating amino acids of a protein, typically with alanine (alanine scanning), and determining the effect of each mutation on antibody binding (Onda et al., 2011, Proc. Natl. Acad. Sci. 108 (14):5742-7). A disruption of protein-antibody binding following mutagenesis indicates that the mutated residue is part of a B-cell epitope recognized by the antibody. It has been found that even a single mutation in a B-cell epitope can eliminate binding to a panel of antibodies directed to the protein, and that immunogenicity of a protein can be reduced by the introduction of mutations in a B-cell epitope (Nagata and Pastan, 2009, Advanced Drug Delivery Reviews 61:977-985). However, this approach is also time consuming and labor intensive. Moreover, alanine scanning does not necessarily identify mutations that would provide the greatest reduction in immunogenicity.

Thus, there is a need for a simple, non-labor intensive yet comprehensive method which allows for the identification and elimination of B-cell epitopes.

4. SUMMARY

The present disclosure provides a system that permits the immunogenic contribution of each and every amino acid within an area of interest in a reference antibody to be elucidated. The disclosure provides that an amino acid residue at any, some, or all positions of a reference antibody can be mutated into some or all of the other 19 amino acids and the effect of that mutation on the antibody's immunogenicity evaluated. The effect of the mutations on the antibody's expression level and/or binding to a target molecule can also be evaluated, allowing the identification of antibody variants in which immunogenic regions are eliminated or mitigated yet which retain advantageous properties (e.g., suitable expression levels, binding to target molecule). Accordingly, the present disclosure provides methods for reducing the immunogenicity of an antibody. The methods are based on screening for and identifying antibody variants with reduced binding to anti-idiotypic antibodies. Reduction of binding to anti-idiotypic antibodies correlate with reduced in vivo immunogenicity (see, e.g., Nagata and Pastan, 2009, Advanced Drug Delivery Reviews 61:977-985).

The methods of the disclosure generally comprise the steps of (a) contacting a host cell library with an anti-idiotypic antibody that specifically binds to the reference antibody, the reference antibody being a monoclonal antibody that binds to a target molecule, the host cell library comprising mammalian host cells that each express on the cell surface an antibody variant differing from the reference antibody by a single amino acid point mutation; (b) identifying a population of cells in said host cell library that express antibody variants that display decreased binding to the anti-idiotypic antibody relative to the reference antibody; and (c) identifying an antibody variant that is enriched in the population, thereby identifying a variant of a reference antibody with reduced immunogenicity. In certain aspects, the methods entail subjecting the host cell library to flow cytometry and sorting the population from the host cell library using, for example, fluorescent activated cell sorting (FACS).

In certain aspects, the methods further comprise a step of determining whether the antibody variant having reduced immunogenicity binds to the target molecule at a level which is substantially equal to or better than the reference antibody and/or is expressed at a level which is substantially equal to or better than the expression level of the reference antibody. In specific embodiments, binding and expression are determined by flow cytometry, magnetic bead sorting, BIAcore, FACS, ELISA, AlphaLisa, or KinExA, and are determined before, simultaneously with, or after the identification of antibody variants having reduced immunogenicity.

The methods described herein have been applied to the anti-TNF-α antibody D2E7 (also known as Adalimumab). Variants of D2E7 with reduced binding to one, two, or three different anti-idiotypic antibodies were identified. The present disclosure provides anti-TNF-α antibodies with CDR sequences related to those of D2E7, but which have at least one substitution that reduces the binding to anti-Id antibodies. Such variants are sometimes referred to herein as "reduced immunogenicity" variants.

Anti-TNF-α antibodies of the disclosure comprise six CDRs having amino acid sequences corresponding to SEQ ID NO:5 (CDR-H1), SEQ ID NO:6 (CDR-H2), SEQ ID NO:7 (CDR-H3), SEQ ID NO:8 (CDR-L1), SEQ ID NO:9 (CDR-L2) and SEQ ID NO:10 (CDR-H3), and have at least one substitution selected from G5F in CDR-L1, G5I in CDR-L1, G5V in CDR-L1, G5W in CDR-L1, G5Y in CDR-L1, R7I in CDR-L1, R7T in CDR-L1, R7V in CDR-L1, N8A in CDR-L1, N8D in CDR-L1, N8E in CDR-L1, N8G in CDR-L1, N8L in CDR-L1, N8M in CDR-L1, N8Q in CDR-L1, N8R in CDR-L1, N8T in CDR-L1, A1I in CDR-L2, A1T in CDR-L2, A1V in CDR-L2, T4D in CDR-L2, R2G in CDR-L3, N4F in CDR-L3, N4M in CDR-L3, N4W in CDR-L3, N4Y in CDR-L3, R5L in CDR-L3, R5N in CDR-L3, R5W in CDR-L3, R5Y in CDR-L3, T9Y in CDR-L3, D1S in CDR-H1, Y2A in CDR-H1, Y2C in CDR-H1, Y2K in CDR-H1, Y2M in CDR-H1, Y2R in CDR-H1, Y2S in CDR-H1, Y2V in CDR-H1, H5C in CDR-H1, H5D in CDR-H1, H5E in CDR-H1, H5S in CDR-H1, H5T in CDR-H1, T3A in CDR-H2, T3G in CDR-H2, T3N in CDR-H2, W4A in CDR-H2, W4F in CDR-H2, W4H in CDR-H2, W4L in CDR-H2, W4M in CDR-H2, W4V in CDR-H2, N5G in CDR-H2, S6D in CDR-H2, S6L in CDR-H2, I9K in CDR-H2, D10L in CDR-H2, Y11A in CDR-H2, Y11C in CDR-H2, Y11E in CDR-H2, Y11F in CDR-H2, Y11G in CDR-H2, Y11H in CDR-H2, Y11I in CDR-H2, Y11K in CDR-H2, Y11L in CDR-H2, Y11M in CDR-H2, Y11N in CDR-H2, Y11Q in CDR-H2, Y11R in CDR-H2, Y11S in CDR-H2, Y11V in CDR-H2, Y11W in CDR-H2, A12Y in CDR-H2, D13N in CDR-H2, V15D in CDR-H2, V15L in CDR-H2, V15M in CDR-H2, V15Q in CDR-H2, V15T in CDR-H2, E16F in CDR-H2, E16H in CDR-H2, E16K in CDR-H2, E16R in CDR-H2, E16T in CDR-H2, E16W in CDR-H2, G17A in CDR-H2, G17C in CDR-H2, G17E in CDR-H2, G17H in CDR-H2, G17I in CDR-H2, G17K in CDR-H2, G17L in CDR-H2, G17M in CDR-H2, G17N in CDR-H2, G17P in CDR-H2, G17Q in CDR-H2, G17R in CDR-H2, G17S in CDR-H2, G17T in CDR-H2, G17Y in CDR-H2, V1G in CDR-H3, V1R in CDR-H3, V1W in CDR-H3, L4T in CDR-H3, L4V in CDR-H3, T6V in CDR-H3, S9K in CDR-H3, S9W in CDR-H3, S9Y in CDR-H3, and D11V in CDR-H3. The six CDRs altogether can have up to 8, up to 7, up to 6, up to 5, or up to 4 amino acid substitutions as compared to CDR sequences of Adalimumab. In certain aspects, each CDR can have up to 4, up to 3, or up to 2 substitutions as compared to the CDRs of Adalimumab. In specific embodiments, the anti-TNF-α antibodies of the disclosure have one or more combinations of amino acid substitutions in which the heavy chain substitution(s), if present, comprise at least one of (a) Y2K in CDR-H1; (b) Y2M in CDR-H1; (c) Y2K in CDR-H1 and T6V in CDR-H3; (d) Y2K in CDR-H1, V1G in CDR-H3 and T6V in CDR-H3; (e) V1W in CDR-H3; and (f) V1G in CDR-H3 and T6V in CDR-H3, and in which the light chain substitution(s), if present, comprise at least one of (a) G5S in CDR-L1 and A11S in CDR-L1; (b) R7I in CDR-L1; (c) G5S in CDR-L1, R7T in CDR-L1 and A11S in CDR-L1; and (d) G5S in CDR-L1, R7I in CDR-L1 and A11S in CDR-L1. In specific embodiments, the antibodies of the disclosure comprise a combination of amino acid substitutions selected from those set forth in FIG. 22.

The anti-TNF-α antibodies of the disclosure preferably have reduced binding to one, two, three, four, five, or all six of the Adalimumab anti-Idiotypic antibodies 5A1, 10F8, 7A11, 1H11, 6A11, and 10B7.

The present disclosure further relates to nucleic acid molecules encoding the anti-TNF-α antibodies of the disclosure and host cells comprising them.

The present disclosure further relates to pharmaceutical compositions comprising the anti-TNF-α antibodies of the disclosure and methods of treating a human patient suffering from an immune disorder by administering the anti-TNF-α antibodies or pharmaceutical compositions containing them. In certain aspects, the immune disorder treated is rheumatoid arthritis (RA) (including moderate to severe RA in adults), juvenile idiopathic arthritis (JIA) (including moderate to severe polyarticular JIA in patients 4 years of age and older), psoriatic arthritis (PsA) (including PsA in adults), ankylosing spondylitis (AS) (including AS in adults), Crohn's disease (CD) (including moderate or severe CD in adults), chronic plaque psoriasis (Ps) (including moderate to severe chronic plaque psoriasis in adults), or axial spondyloarthritis (axSpA) (including severe axSpA in adult patients who have no X-ray evidence of structural damage).

5. BRIEF DESCRIPTION OF THE FIGURES

FIGS. 1A-1C: FIG. 1A provides the translated amino acid sequences of the synthetic D2E7 (Adalimumab, HUMIRA) variable heavy ($V_H$) and variable light ($V_L$) fragments. FIG. 1B provides the CDR amino acid sequences of the D2E7 $V_H$ and $V_L$ fragments. FIG. 1C provides the nucleotide sequences of the D2E7 $V_H$ and D2E7 $V_L$ fragments (SEQ ID NO:1 and SEQ ID NO:3, respectively).

FIG. 2: provides a list of beneficial mutations in D2E7-$V_L$ that will lead to a neutral binding to TNF-α and a decreased binding to anti-Id 5A1 (a), 10F8 (b), or 7A11 (c). Amino acid positions are given both in the context of the individual CDRs and in Kabat numbering. FIG. 2 discloses SEQ ID NOS.:8-10, respectively, in order of appearance.

FIGS. 3A-3B: FIG. 3A provides a list of beneficial mutations in D2E7-$V_H$ CDR-H1 and CDR-H2 that will lead to a neutral binding to TNF-α and a decreased binding to anti-Id 1H11 (d), 6A11 (e), or 10B7 (f). FIG. 3B provides a list of beneficial mutations in D2E7-$V_H$ CDR-H3 that will lead to a neutral binding to TNF-α and a decreased binding to anti-Id 1H11 (d), 6A11 (e), or 10B7 (f). Amino acid positions are given both in the context of the individual CDRs and in Kabat numbering. FIG. 3A discloses SEQ ID NOS.:5-6, respectively, in order of appearance. FIG. 3B discloses SEQ ID NO:7.

FIG. 4 provides the structure of D2E7 in vectors pYA206 and pCW600.

FIG. 5 provides a titration plot of human TNF-α on cell surface-expressed WT D2E7 Fab.

FIG. 6 provides a titration plot of anti-idiotype (anti-Ids) binding to cell-surface expressed WT-D2E7 Fab.

FIGS. 7A-7B: FIG. 7A provides FACS sorting profiles for wild-type D2E7 stained with TNF-α. FIG. 7B provides FACS sorting profiles for the $V_H$ point mutation library stained with TNF-α.

FIGS. 8A-8B provides FACS sorting profiles for wild-type D2E7 and the $V_H$ point mutation library stained with 1H11.

FIG. 9 provides silent codon mutation D2E7 Enrichment Ratios by position. Amino acid positions are given in the context of the individual CDRs.

FIG. 10 provides a plate map of D2E7 sub-libraries. Amino acid positions are given both in the context of the individual CDRs and in Kabat numbering. FIG. 10 discloses SEQ ID NOS.:8-10 and 5-7, top to bottom, left to right, respectively, in order of appearance.

FIG. 11 provides FACS profiles of D2E7 mutant sub-libraries and wild-type controls.

FIG. 12 provides FACS profiles of D2E7 mutant sub-libraries and wild-type controls.

FIGS. 13A-13D provides a space-filling model of D2E7 heavy chain variable region. Panels A, B, and C show light chain CDR 1, 2, and 3 in grey, respectively. Panel D shows the epitope of anti-Id anti-Id 1H11 in grey. The $V_H$ sequence (SEQ ID NO:2) as depicted below shows the CDR underlined and the positions that are important for binding to anti-Id 1H11 in bold, double-underline text. Each of the three CDRs contributes one or more amino acids to the epitope.

(SEQ ID NO: 2)
EVQLVESGGGLVQPGRSLRLSCAASGFTFDDYAMHWVRQAPGKGLEWV

SAITWNSGHIDYADSVEGRFTISRDNAKNSLYLQMNSLRAEDTAVYYC

AKVSYLSTASSLDYWGQGTLVTVSS

FIGS. 14A-14D provides a space-filling model of D2E7 light chain variable region. Panels A, B, and C show light chain CDR 1, 2, and 3 in grey, respectively. Panel D shows the epitope of anti-Id 5A1 and 10F8 in grey. The $V_L$ sequence (SEQ ID NO:4) as depicted below shows the CDR underlined and the positions that are important for binding to anti-Id 5A1 and 10F8 are in bold, double-underline text. Each of the three CDRs contributes one or more amino acids to the epitope.

(SEQ ID NO: 4)
DIQMTQSPSSLSASVGDRVTITCRASQGIRNYLAWYQQKPGKAPKLLIYA

ASTLQSGVPSRFSGSGSGTDFTLTISSLQPEDVATYYCQRYNRAPYTFGQ

GTKVEIK

FIG. 15 provides one-point FACS analysis of D2E7-$V_H$ CDR1-2 mutants.

FIG. 16 provides a D2E7 representative positional analysis.

FIG. 17 provides average 1H11 Enrichment Ratios by position.

FIG. 18 provides average 5A1 Enrichment Ratios by position.

FIG. 19 provides average 10F8 Enrichment Ratios by position.

FIGS. 20A-20B shows the impact of anti-TNF-α antibody mutations on binding to anti-Adalimumab antibodies in serum samples from four commercial donors. Amino acid positions are given in Kabat numbering. VL-SS refers to a VL having the substitutions G28S and A34S in CDR-L1 (Kabat numbering), corresponding to the G5S+A11S combination in CDR-L1.

FIG. 22 shows binding data for variants with multiple amino acid substitutions. VL-SS refers to a VL having the substitutions G28S and A34S in CDR-L1 (Kabat numbering), corresponding to the G5 S+A11S combination in CDR-L1.

6. DETAILED DESCRIPTION

Figure 4:
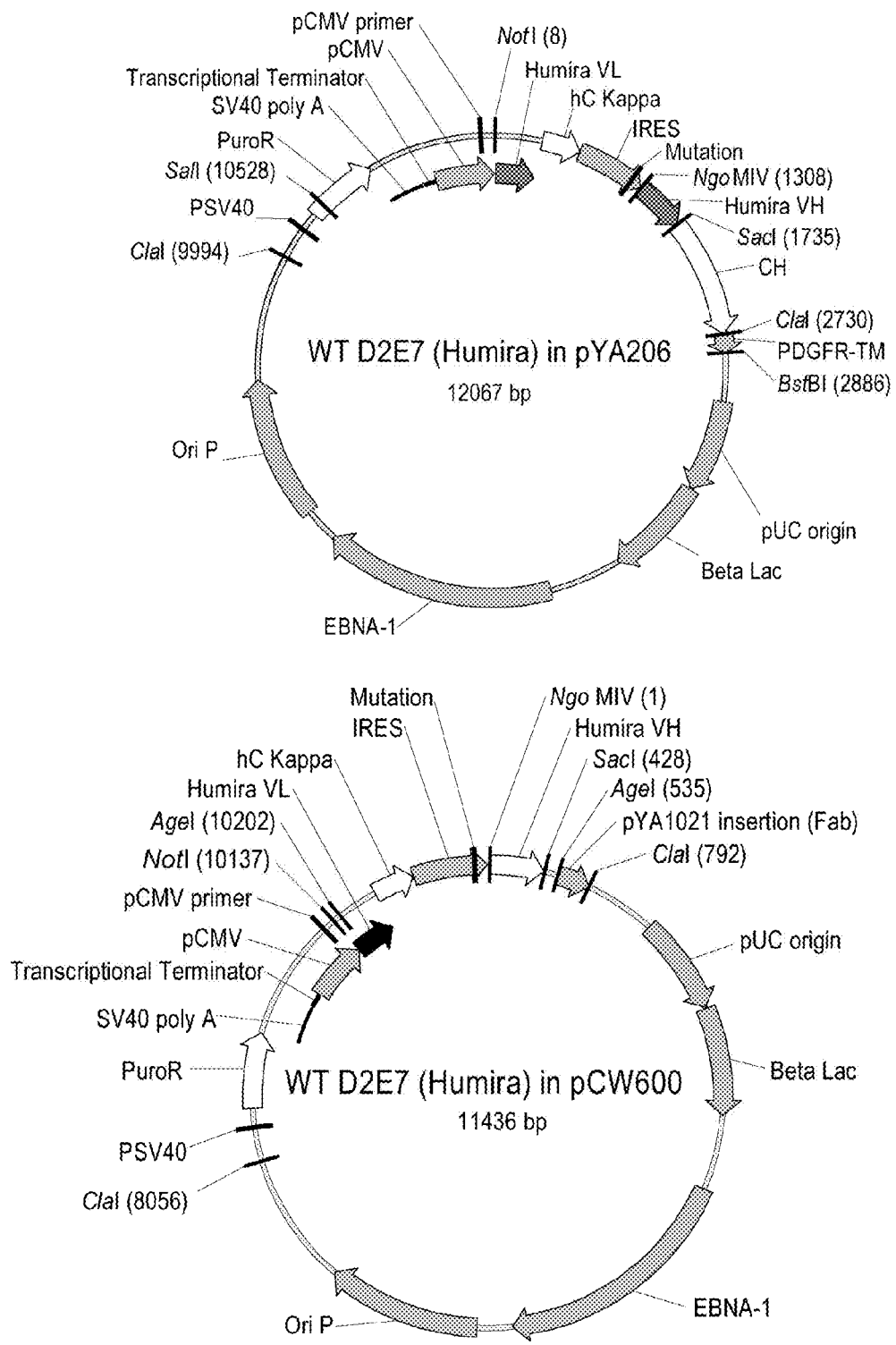

6.1. Methods of Identifying Antibodies with Reduced Immunogenicity

The present disclosure further provides a system that permits the immunogenic contribution of each and every amino acid in a region of interest within an antibody of interest (the reference antibody) to be elucidated. The methods entail subjecting the reference antibody to a comprehensive mutagenesis in one or more regions (e.g., one or more of CDR-L1, CDR-L2, CDR-L3, CDR-H1, CDR-H2, CDR-H3, FR-L1, FR-L2, FR-L3, FR-H1, FR-H2, FR-H3, and FR-H4), and evaluating the effect of the mutations on binding to an anti-idiotypic antibody (an "anti-Id"). The methods described herein resulted in the identification of the variant anti-TNF-α antibodies with reduced immunogenicity described above.

Library Design and Construction:

An antibody library is designed that contain every possible single amino acid substitution at every possible position in a desired region or domain of a reference antibody for identifying the effect (good, bad or neutral) of a mutation on binding to an anti-Id antibody. A library of antibody variants is then constructed, for example using "randomized NNK codons" to generate the single amino acid variants, where "N" refers to any base (e.g., A, C, G, or T) and "K" refers to either G or T. The NNK randomization scheme can encode 32 different codons covering all 20 naturally occurring amino acids. Amino acid residues at each position of the antibody can be mutated to any one of the 19 amino acids that is different than the wild type amino acid at the same position, resulting in single amino acid point mutation in the antibody. The end result is an antibody variant library encompassing groups of multiple antibodies having one residue that varies from member to member in the library. The overall complexity of the library can be between about 50-10,000 members (e.g., 50, 100, 500, 1000, 1500, 2000, 2500, 3000, 3500, 4000, 4500, 5000, 5500, 6000, 6500, 7000, 7500, 8000, 8500, 9000, 9500, or 10,000 members), between about 1000-5000 members, or about 1000 members, based on the number of amino acids targeted for mutation. Irrespective of the size and complexity of the library, the methods described herein allow simultaneous screening and simultaneous sequencing of all the members of the library.

As a non-limiting example, to identify specific antibody variants with decreased immunogenicity compared to the reference antibody, the amino acid residues in the complementarity determining regions (CDRs) are potential targets for mutation. Elimination or mitigation of a B-cell epitope can produce an antibody with reduced immunogenicity. Typically, about 50 to 60 CDR amino acid positions can be considered and identified for mutation. A set of synthetic DNA fragments can be designed and constructed, which encode for wild type parental $V_H$ or $V_L$ and all possible single amino acid antibody variants. The randomized NNK codons described above can be used to generate the single amino acid antibody variants. Thus, amino acid residues at each position within the CDR can be mutated, resulting in single amino acid point mutations along the selected CDR region. The end result is antibody variant libraries that are groups of multiple antibodies having one residue that varies from member to member in the library. In this example, the library has approximately 1000-1300 members, where each of the 50 to 60 or 65 CDR amino acid positions in the selected region is substituted with one of the 19 naturally occurring amino acids for a total of 20 different amino acids at any given position (i.e., 50×20=1000; 60×20=1200; or 65×20=1300).

Expression of Antibody Variants:

Following library construction, the second step is to express the library of antibody variants for sorting by cell surface display. The library of variants can be expressed using display-based methods such as, for example, phage display, yeast display, bacterial display, and ribosome display, and are preferably expressed in mammalian cells to ensure proper folding and posttranslational modification of the expressed variants.

For mammalian expression, the transmembrane domains used to tether and display tetrameric immunoglobulin molecules on the cell surface can be any transmembrane domain capable of removal via enzymatic, chemical, or photolytic cleavage. In some embodiments, the transmembrane domain is flanked by cleavage sites that are recognized and cleaved by a cleaving enzyme. For example, the cleaving enzyme can be a lipase, an esterase, a phosphatase, a glycosidase, or a carboxypeptidase. In some embodiments, the transmembrane domain comprises an oligonucleotide or oligonucleotide analog having a sequence that is recognized and cleaved by a nuclease such as a ribonuclease (RNase) or a deoxyribonuclease (DNase). In some embodiments, the transmembrane domain comprises a peptide or peptide analog that is recognized and cleaved by a protease.

In some embodiments, mRNA splicing can be used to produce immunoglobulins with or without the transmembrane domain (see, e.g., U.S. Pat. No. 7,947,495, herein incorporated by reference in its entirety).

In other embodiments, the transmembrane domain is flanked by recombinase recognition sites that are recognized by a recombinase. Examples of recombinase recognition sites include, but are not limited to, lox sites, att sites, dif sites and frt sites. For reviews of recombinases, see, e.g., Sauer, 1994, *Curr. Opin. Biotech.* 5:521-527; Landy, 1993, Curr. Opin. Biotech. 3:699-707; Sadowski, 1993, *FASEB* 7:760-767; and U.S. Patent Publication No. 20040115814.

Transmembrane domains for use in the compositions and methods described herein can be derived from type I, type II, and type III membrane proteins (see, e.g., Chesnut et al., 1996, *J. Imm. Methods*, 193:17-27; Wahlberg et al., 1997, *J. Cell Biol.*, 137:555-562; Liao, 2001, *Biotech. and Bioeng.*, 73:313-323; and U.S. Pat. Nos. 5,264,357 and 6,686,168). The transmembrane domains described herein can be used to produce immunoglobulin-transmembrane domain fusion proteins comprising full length antibodies (e.g., IgG) or fragments thereof which are tethered to and displayed on the surface of cells expressing the fusion proteins.

Transmembrane domains that are particularly useful in the compositions and methods described herein include, but are not limited to, a platelet derived growth factor receptor (PDGF-R) transmembrane domain (see, e.g., Chesnut et al., 1996, *J. Imm. Methods*, 193:17-27), a B7-1 transmembrane domain (see, e.g., Chou et al., 1999, *Biotech. & Bioeng.*, 65(2):160-169), and an asialoglycoprotein receptor (AS-GPR) transmembrane domain (see, e.g., Liao, 2001, *Biotech. & Bioeng.*, 73:313-323). In some embodiments, the cell surface tether domain refers to a GPI signal sequence which directs anchoring of the immunoglobulin to the cell-surface via a glycosidylphosphatidylinositol (GPI) linker (see, e.g., Medof et al., 1987, *Proc. Natl. Acad. Sci. USA*, 84:2007-2011; and U.S. Pat. Nos. 5,109,133 and 5,264,357). In certain instances, the GPI signal sequence is from human decay-accelerating factor (DAF). In other embodiments, the cell surface transmembrane domain anchor is from an immunoglobulin protein.

The mammalian display vectors can be used to display intact antibodies, although antibody fragments such as, for example, Fc, Fab', F(ab)'$_2$, and single chain Fv, can also be displayed. Both heavy and light chains can be encoded as a single transcript by virtue of the use of an internal ribosome entry site (IRES) element, which joins the polynucleotide sequence encoding the variable and constant light chains to the polynucleotide encoding the variable and constant heavy chains.

In an embodiment, the mammalian display vectors comprise a removable GPI anchor fused to the C-terminus of the heavy chain constant region to facilitate the isolation of antibodies with desired binding characteristics and biological activities. When present, the GPI anchor enables immunoglobulin molecules to be displayed on the surface of the mammalian host cell. Removal of the GPI anchor by digestion with appropriate restriction endonucleases allows conversion from membrane-bound to soluble immunoglobulin molecules.

Examples of suitable mammalian host cells include, but are not limited to, HeLa cells (HeLa S3 cells, ATCC CCL2.2), Jurkat cells, Raji cells, Daudi cells, human embryonic kidney cells (293-HEK; ATCC 293c18, ATCC CRL 1573), African green monkey kidney cells (CV-1; Vero; ATCC CRL 1587), SV40-transformed monkey kidney cells (COS-1; ATCC CRL 1650), canine kidney cells (MDCK; ATCC CCL 34), baby hamster kidney cells (BHK-21, BHK-570; ATCC CRL 8544, ATCC CRL 10314), Chinese hamster ovary cells (CHO-K1; ATCC CCL61; CHO DG44 (Chasin et al., 1986, *Som Cell Molec Genet*, 12, 555)), and other rodent cell lines such as NSO, SP2/O, GH1 (ATCC CCL82), H-4-II-E (ATCC CRL 1548), and NIH-3T3 (ATCC CRL 1658).

In one embodiment, the methods and vectors described in U.S. Pat. No. 7,947,495, herein incorporated by reference in its entirety, can be used. The mammalian cell surface display system includes self-replicating vectors and mammalian cells. Self-replicating mammalian vectors typically comprise: (1) a self-replicating origin of replication; (2) at least one eukaryotic promoter; (3) a fixed or removable transmembrane domain; (4) a light chain constant region; (5) a heavy chain constant region; (6) restriction sites for the insertion of light and heavy chain variable regions; (7) an internal ribosome entry site (IRES); and (8) at least one selectable marker. In addition, the vectors can comprise a prokaryotic origin of replication, a transcriptional terminator, a polyadenylation signal and/or leader sequences, as well as other sequences necessary for expression in eukaryotic host cells. Once transformed, the host cells are incubated under conditions that allow expression of the antibodies. The resulting plasmids can be readily recovered from cells as described (see, e.g., Hirt, 1967, *J. Mol. Biol.*, 26, 365-369).

In addition to the above techniques, yeast surface display library can be employed for cell surface display of variant antibody libraries. Yeast surface display technology (reviewed by Boder and Wittrup, 2000, *Methods in Enzymology* 328:430-444, which is incorporated herein by reference in its entirety) allows antibody libraries to be expressed on the yeast cell wall in a form accessible for interacting with a labeled molecule for analysis in cell sorting methods. In one embodiment, the variants are expressed as fusion proteins with all or a portion of the yeast AGA2 protein, which become displayed on the surface of the yeast cell wall, for sorting according to the methods described below. See, e.g., Boder et al., 1997, *Nat. Biotechnol.* 15:553-557 and Feldhaus et al., 2003, Nat. Biotechnol. 21:163-170.

Phage display of antibody variants can also be used. Antibody chains can be expressed as fusion proteins with a phage coat protein from the outer surface of the phage. Thereafter, display packages can be screened for display of antibodies binding to a target. In one embodiment, the antibody variants are displayed in a monovalent fashion from filamentous phage particles as fusions to the gene III product of M13 packaged within each particle and expressed on the exterior of the phage. Antibody phage display methods are known to those skilled in the art and are described, for example, in Hoogenboom, "Overview of Antibody Phage-Display Technology and Its Applications," from *Methods in Molecular Biology: Antibody Phage Display Methods and Protocols* (2002) 178:1-37 (O'Brien and Aitken, eds., Human Press, Totowa, N.J.).

In another embodiment, ribosome display technology (see Hanes et al., 2000, *Meth. Enzymol.* 328: 403-430; Pluckthun et al., 2000, *Adv. Prot. Chem.* 55:367-403; Lipovsek and Pluckthun, 2004, *J. Immunological Methods* 290:51-67) is used to express variant antibodies. Ribosome display technology incorporates in vitro translation and covalent or non-covalent linkage between genotype, such as RNA, and the encoded phenotype, such as a variant antibody, to select for variant antibodies that have reduced binding to anti-Id antibodies. The library is made by synthesizing a DNA pool of diverse sequences that are then transcribed to produce a pool of mRNAs. In vitro translation is used to generate the encoded polypeptides or proteins displayed, and desirable binding interactions are selected using an immobilized binding partner. mRNA encoding the binding entities can be used to make cDNA, which can then be amplified and the process may be repeated to enrich the population for genes encoding variant antibodies with desired characteristics. The selected proteins can be identified by cloning individual coding sequences and DNA sequencing.

A bacterial display system can also be used to express variant antibodies. See, e.g., Skerra et al., 1988, *Science* 240: 1038-1041; Better et al., 1988, *Science* 240:1041-1043; Harvey et al., 2004, *Proc. Nat'l Acad. Sci. USA* 101(25):9193-9198; and Mazor et al., 2007, *Nat. Biotechnol.* 25(5):563-565.

Library Sorting:

Host cells displaying expressed antibody variants can be sorted using affinity-based enrichment assays. The variant antibodies can be sorted based on their (1) loss of binding to an anti-Id, (2) optionally, retention of binding to the target antigen and (3) optionally, expression levels. Anti-Ids are antibodies directed against the variable regions of other antibodies. For this reason, the antigen binding site of an anti-Id can be similar to the target molecule bound by the antibody recognized by the anti-Id. Methods of making anti-Ids are known in the art, and generally entail using the antibody of interest (e.g., the reference antibody) as an immunogen to generate antibodies by traditional means, such as those described below for the reference antibody. The anti-Id antibodies can be monoclonal of either human or animal origin.

Examples of assays suitable for use in sorting the antibody variants include, but are not limited to, fluorescence-activated cell sorting (FACS), magnetic bead sorting, the CellSpot™ antibody screening technology from Trellis Bioscience, Inc. (South San Francisco, Calif.), and/or the ClonePix FL mammalian cell clone screening apparatus from Genetix Ltd. (Hampshire, United Kingdom).

For FACS sorting, cells are incubated with a fluorescently labeled antibody (e.g., an anti-Id or an antibody that detects a common epitope in the non-mutagenized portions of the variants) or target antigen at a concentration close to the dissociation constant ($K_D$) for the reference antibody affinity, for maximal discrimination between the reference antibody and variants with similar affinities. Stained cells are sorted into one or more subpopulations in such a way that the frequencies of variants with a property of interest are either increased or decreased in the relevant subpopulation.

Sorting for anti-Id binding can be performed using any of the above-described methods. Generally, cells expressing antibody variants are incubated with an anti-Id and sorted by amount of bound anti-Id. A baseline binding value can be obtained from cells expressing the reference antibody, and cells that display decreased binding to the anti-Id can be identified by sorting the cells into subpopulations having bound anti-Id above or below the baseline value.

Optionally, cells expression antibody variants are also sorted based on expression levels. The total amount of fluorescent antibody or antigen bound to a cell expressing an antibody variant during, e.g., FACS, is related to both the binding affinity and the total amount of variant antibody displayed. The amount of variant antibody displayed can vary from clone to clone. Thus, in certain instances, cells expressing the variant antibodies of interest, e.g., a full length IgG tethered to the cell surface via a transmembrane domain anchor, can be sorted using FACS using a fluorescently labeled antibody against the immunoglobulin (e.g., anti-IgG antibody) (in addition to sorting for anti-Id binding). The different antibodies used for detection of different properties, e.g., the anti-Id and the anti-IgG antibody used to detect expression levels, are typically labeled with fluorophores having different excitation and/or emission spectra, thereby providing a two-color detection system.

Cells can also be sorted for target binding. Typically, it will be desirable to select an antibody variant that retains binding to the target, e.g., a variant with approximately equal or greater binding to the target molecule as compared to the reference antibody. Libraries co-stained with anti-Id and target molecule can be sorted by FACS into two subpopulations: a first population above a certain threshold for target binding, and a second population double sorted for target binding as well as decreased anti-idiotype binding. The different molecules used for detection of different properties, e.g., the anti-Id and target molecule, are typically labeled with fluorophores having different excitation and/or emission spectra, thereby providing a two-color detection system.

In yet other embodiments, cells can be sorted for anti-Id binding, expression levels and target binding. In these embodiments, a three-color detection system using three distinguishable labels can be used.

When double or triple staining is used for simultaneous sorting for anti-Id binding and expression levels and/or target binding, the labeled target and labeled antibodies are typically labeled with fluorophores having different excitation and/or emission spectra, thereby providing a two-color or three-color detection system. Sorting into different populations can also be carried out serially. For example, cells sorted into a subpopulation having reduced binding to the anti-Id can be sorted into further subpopulations based upon target binding and expression levels, the sorting based target binding and expression levels occurring simultaneously or sequentially. In other embodiments, variants identified during sorting for anti-idiotypic antibody binding (and host cells expressing them) are characterized for target binding using an independent validation methods described below.

Analysis of the Sorted Populations:

Following sorting into subpopulations, the frequency of each antibody variant in each subpopulation can be determined by sequencing the plasmids encoding the variants. A preferred DNA sequencing method of the disclosure is the "massively parallel sequencing" or "massively parallel pyrosequencing" (see, e.g., U.S. Pat. Nos. 6,787,308; 6,833, 246; 6,897,023; 6,956,114; 7,057,026; 7,115,400, 7,211,390; and 7,232,656). This method allows rapid and inexpensive sequencing of DNA and accelerates the identification of specific antibody variants with the desired activity or characteristics.

Subsequent to sequencing, statistical analysis of the sequences can be performed to identify desired variants. Such analysis can include computer analysis of the raw DNA sequences. The raw DNA sequences can be translated into protein sequence, aligned and compared with the reference antibody to identify the mutations. The frequency of each amino acid observed at each position can be tabulated for the type of category (e.g., decreased immunogenicity, and increase, decrease, or neutral expression or affinity for target molecule) and compared with the reference antibody. Variants with the desired activity, such as, e.g., those which reduce immunogenicity, retain expression, and/or retain the binding to the target molecule, will be enriched in the selected population, while variants with undesired activities will be depleted in the selected population.

An Enrichment Ratio (ER) can be calculated for each variant which provides a measure of the extent of enrichment or depletion of the variant in a population as compared to other variants and/or the reference antibody. In embodiments where cells are sorted based on (a) expression levels above a certain threshold and (b) low binding to an anti-idiotype (the "sorted" population), the number of times a mutation is found at a given position is normalized for the number of times that position was sequenced and expressed as a frequency per 1000 sequences. Then the frequency of the mutation in the sorted population is divided by the frequency in the expressed population to give the Enrichment Ratio (ER) which indicates whether the mutation has been enriched or depleted in the sorted population compared to the expressed population, and to what extent. Mutations that are enriched in the sorted population will have decreased binding to the anti-idiotype, while mutations that are depleted will have increased binding to the anti-idiotype. Similarly, Enrichment Ratios can be calculated for each variant sorted according increased, decreased, or similar (neutral) affinity to target.

In embodiments where cells are sorted only for decreased binding to anti-idiotype, e.g., where the cells are not simultaneously sorted for expression levels, an Enrichment Ratio can be determined by dividing the frequency of the mutation in a subpopulation having bound anti-idiotype below a baseline value determined from cells expressing the reference antibody by the frequency of the mutation in a subpopulation having bound anti-idiotype at or above the baseline value.

Validation of Individual Variants:

The binding characteristics of individually expressed variant polypeptides can be analyzed using a variety of techniques to confirm their behavior in the context of a library. These techniques include BIAcore, FACS, ELISA, AlphaLisa, and KinExA. BIAcore assays determine binding using Surface Plasmon Resonance (SPR), an optical phenomenon allowing detection of unlabeled interactants and can be used to determine the binding affinity of individual antibody variants (e.g., U.S. Pat. App. No. 2008/0274114; and Che et al., 2009, *J. Pharm. and Biomed. Analysis* 50(2):183-188). AlphaLISA can be used to determine the binding affinity of individual variants to a target molecule (see, for example, Ullman et al., 1996, *Clinical Chemistry*, 42(9):1518-1526; and Hideharu et al., 2007, *Cancer Science* 98(8):1275-1280). KinExA (kinetic exclusion assay) measures the concentration of uncomplexed receptor (R) molecule in a mixture of receptor, ligand (L), and LR complex. The concentration of uncomplexed R is measured by exposing the solution phase mixture to solid phase immobilized L for a very brief period of time. The "contact time" between the solution phase mixture and the solid phase immobilized L is kept short enough that dissociation of LR complex is insignificant. When the possibility of significant dissociation of LR complex is kinetically excluded, only uncomplexed ("free") R can bind to the solid phase. The amount of free R that binds to the solid phase (measured by fluorescence emission from a secondary label) is directly proportional to the concentration of free R in the solution phase sample KinExA can also be used to determine the binding affinity of individual variants to a target molecule (see, for example, U.S. Pat. App. No. 2008/0274114; and Darling et al., 2004, *ASSAY and Drug Development Technologies* 2:647-657).

6.2. Variant Anti-TNF-α Antibodies

The methods described above have been applied to the anti-TNF-α antibody D2E7, also known as adalimumab, to identify variants with a reduced affinity for an anti-idiotypic antibody as compared to D2E7. Variants that display reduced affinity for anti-idiotypic antibodies are referred to as "reduced immunogenicity" variants.

In certain aspects, the present disclosure provides anti-TNF-α antibodies having reduced immunogenicity as compared to D2E7. The anti-TNF-α antibodies of the disclosure typically have one or more amino acid substitutions in their CDRs as compared to the CDRs of D2E7, wherein said at least one or more substitutions reduces the immunogenicity of the antibody as compared to D2E7. In certain embodiments, the reduced immunogenicity results from eliminating or mitigating one or more B-cell epitopes.

The amino acid sequences of the heavy and light chain variable regions of D2E7 are represented by SEQ ID NO:2 and SEQ ID NO:4, respectively, and encoded by SEQ ID NO:1 and SEQ ID NO:3, respectively. The amino acid sequences of the heavy and light chain variable regions are also depicted in FIG. 1A. The amino acid sequences of the CDRs of D2E7, and their corresponding identifiers, are presented in FIG. 1B. The nucleotide sequences of the heavy and light chain variable regions of D2E7, as published in U.S. Pat. No. 6,090,382, are shown in FIG. 1C. Any other nucleotide sequences encoding SEQ ID NO:2 or SEQ ID NO:4 can be used in the compositions and methods of the present disclosure in lieu of the published sequences.

In certain aspects, the anti-TNF-α antibodies of the disclosure having reduced immunogenicity have comparable or improved binding to TNF-α relative to D2E7. Affinity can be tested, for example, by the validation methods described in Section 6.1.

Exemplary substitutions yielding anti-TNF-α antibodies with eliminated or mitigated B-cell epitopes and having lower immunogenicity as compared to D2E7 are listed in FIGS. 2 and 3 (i.e., FIGS. 3A-3B). Suitable substitutions include G5F in CDR-L1, G5I in CDR-L1, G5V in CDR-L1, G5W in CDR-L1, G5Y in CDR-L1, R7I in CDR-L1, R7T in CDR-L1, R7V in CDR-L1, N8A in CDR-L1, N8D in CDR-L1, N8E in CDR-L1, N8L in CDR-L1, N8M in CDR-L1, N8Q in CDR-L1, N8R in CDR-L1, A1I in CDR-L2, A1T in CDR-L2, A1V in CDR-L2, T4D in CDR-L2, R2G in CDR-L3, N4F in CDR-L3, N4M in CDR-L3, N4W in CDR-L3, N4Y in CDR-L3, R5L in CDR-L3, R5N in CDR-L3, R5W in CDR-L3, R5Y in CDR-L3, D1S in CDR-H1, Y2A in CDR-H1, Y2C in CDR-H1, Y2K in CDR-H1, Y2M in CDR-H1, Y2R in CDR-H1, Y2S in CDR-H1, Y2V in CDR-H1, H5C in CDR-H1, H5D in CDR-H1, H5E in CDR-H1, H5S in CDR-H1, H5T in CDR-H1, T3A in CDR-H2, T3G in CDR-H2, W4A in CDR-H2, W4F in CDR-H2, W4H in CDR-H2, W4L in CDR-H2, W4M in CDR-H2, W4V in CDR-H2, N5G in CDR-H2, S6D in CDR-H2, S6L in CDR-H2, I9K in CDR-H2, D10L in CDR-H2, Y11A in CDR-H2, Y11C in CDR-H2, Y11E in CDR-H2, Y11F in CDR-H2, Y11G in CDR-H2, Y11H in CDR-H2, Y11I in CDR-H2, Y11K in CDR-H2, Y11L in CDR-H2, Y11M in CDR-H2, Y11N in CDR-H2, Y11Q in CDR-H2, Y11R in CDR-H2, Y11S in CDR-H2, Y11V in CDR-H2, Y11W in CDR-H2, A12Y in CDR-H2, D13N in CDR-H2, V15D in CDR-H2, V15L in CDR-H2, V15M in CDR-H2, V15Q in CDR-H2, V15T in CDR-H2, E16F in CDR-H2, E16H in CDR-H2, E16K in CDR-H2, E16T in CDR-H2, E16W in CDR-H2, G17A in CDR-H2, G17C in CDR-H2, G17E in CDR-H2, G17H in CDR-H2, G17I in CDR-H2, G17K in CDR-H2, G17L in CDR-H2, G17M in CDR-H2, G17P in CDR-H2, G17Q in CDR-H2, G17R in CDR-H2, G17S in CDR-H2, G17T in CDR-H2, G17Y in CDR-H2, V1G in CDR-H3, V1R in CDR-H3, V1W in CDR-H3, L4T in CDR-H3, L4V in CDR-H3, T6V in CDR-H3, S9K in CDR-H3, S9W in CDR-H3, S9Y in CDR-H3, and D11V in CDR-H3.

The anti-TNF-α antibodies of the disclosure can comprise any of the substitutions listed in FIGS. 2 and 3, alone or in combination, and, optionally, one or more additional substitutions. Exemplary CDR-L1 substitutions yielding antibodies with eliminated or mitigated T cell epitopes and having lower immunogenicity as compared to D2E7 are listed in Table 11 of U.S. Publication No. 2010/0266613 A1 and PCT International Publication No. 2010/121140, each incorporated by reference in its entirety. Suitable substitutions and combinations of substitutions in CDR-L1 include R7Q; A11S; R7Q+A11S; N8T; N8T+A11S; I6T; A11G; I6T+A11G; Q4G; Q4G+A11S; Q4G+A11G; Q4H; Q4H+ A11S; Q4R; Q4R+A11S; G5S; G5S+A11S; N8S+A11S; I6T+A11S; and N8T+A11G.

Exemplary substitutions yielding antibodies with increased affinity to TNF-α as compared to D2E7 are listed in Tables 12 and 25 of U.S. Publication No. 2010/0266613 A1 and PCT International Publication No. 2010/121140. Suitable substitutions include S3K in CDR-L2, S3R in CDR-L2, S3N in CDR-L2, T4H in CDR-L2, T4Q in CDR-L2, T4V in CDR-L2, T4F in CDR-L2, T4W in CDR-L2, T4Y in CDR-L2; L5R in CDR-L2, L5K in CDR-L2, Q6K in CDR-L2, Q6R in CDR-L2, D1G in CDR-H1, Y2H in CDR-H1, A3G in CDR-H1, and T3N in CDR-H2.

Antibodies of the disclosure can comprise one or more substitutions described in Tables 11-25 of U.S. Publication No. 2010/0266613 A1 and PCT International Publication No. 2010/121140.

The anti-TNF-α antibodies of the disclosure can be monoclonal, genetically engineered and otherwise modified forms of antibodies, including but not limited to chimeric antibodies, humanized antibodies, heteroconjugate antibodies (e.g., bispecific antibodies, diabodies, triabodies, and tetrabodies), and antigen binding fragments of antibodies, including, e.g., Fab', F(ab')$_2$, Fab, Fv, rIgG, and scFv fragments. Moreover, unless otherwise indicated, the term "monoclonal antibody" (mAb) is meant to include both intact molecules, as well as, antibody fragments (such as, for example, Fab, Fab', F(ab')$_2$ and Fv fragments) which are capable of specifically binding to a protein.

Fab and F(ab')$_2$ fragments lack the Fc fragment of intact antibody, clear more rapidly from the circulation of the animal or plant, and may have less non-specific tissue binding than an intact antibody (Wahl et al., 1983, *J. Nucl. Med.* 24:316). The Fab fragment contains the constant domain of the light chain and the first constant domain ($C_H1$) of the heavy chain. Fab' fragments differ from Fab fragments by the addition of a few residues at the carboxyl terminus of the heavy chain $C_H1$ domain including one or more cysteines from the antibody hinge region. F(ab') fragments are produced by cleavage of the disulfide bond at the hinge cysteines of the F(ab')$_2$ pepsin digestion product. An "Fv" fragment is the minimum antibody fragment which contains a complete target recognition and binding site. This region consists of a dimer of one heavy and one light chain variable domain in a tight, noncovalent association ($V_H$-$V_L$ dimer). "Single chain Fv" or "scFv" antibody fragments comprise the $V_H$ and $V_L$ domains of an antibody in a single polypeptide chain, and are also within the scope of the disclosure. Other antibodies encompassed by the disclosure include "single domain antibodies," which are composed of a single $V_H$ or $V_L$ domain that exhibits sufficient affinity to the target molecule. In a specific embodiment, the single domain antibody is a camelid antibody (see, e.g., Riechmann, 1999, *Journal of Immunological Methods* 231:25-38).

The anti-TNF-α antibodies of the disclosure are preferably monoclonal antibodies. The term "monoclonal antibody" as used herein is not limited to antibodies produced through hybridoma technology. The term "monoclonal antibody" refers to an antibody that is derived from a single clone, including any eukaryotic, prokaryotic, or phage clone and not the method by which it is produced. Monoclonal antibodies useful in connection with the present disclosure can be prepared using a wide variety of techniques known in the art including the use of hybridoma, recombinant, and phage display technologies or a combination thereof. The antibodies of the disclosure include chimeric, primatized, humanized, or human antibodies.

The anti-TNF-α antibodies of the disclosure can be bispecific antibodies. Bispecific antibodies are monoclonal, often human or humanized, antibodies that have binding specificities for at least two different antigens. In the present disclosure, one of the binding specificities can be directed towards any two antigens such as a cell-surface protein, receptor, receptor subunit, tissue-specific antigen, virally derived protein, virally encoded envelope protein, bacterially derived protein, or bacterial surface protein, etc.

The anti-TNF-α antibodies of the disclosure include derivatized antibodies. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using ambrx technology (See, e.g., Wolfson, 2006, *Chem. Biol.* 13(10):1011-2).

In yet another embodiment of the disclosure, the anti-TNF-α antibodies can be antibodies whose sequence has been modified to alter at least one constant region-mediated biological effector function relative to the corresponding wild type sequence. For example, in some embodiments, the reference antibodies and/or antibody variants of the disclosure can be modified to reduce at least one constant region-mediated biological effector function relative to an unmodified antibody, e.g., reduced binding to the Fc receptor (FcγR). FcγR binding can be reduced by mutating the immunoglobulin constant region segment of the antibody at particular regions necessary for FcγR interactions (See, e.g., Canfield and Morrison, 1991, *J. Exp. Med.* 173:1483-1491; and Lund et al., 1991, *J. Immunol.* 147:2657-2662). Reduction in FcγR binding ability of the antibody can also reduce other effector functions which rely on FcγR interactions, such as opsonization, phagocytosis and antigen-dependent cellular cytotoxicity ("ADCC").

In other embodiments of the disclosure, a reference antibody and/or antibody variant can be modified to acquire or improve at least one constant region-mediated biological effector function relative to an unmodified antibody, e.g., to enhance FcγR interactions (See, e.g., US 2006/0134709). For example, a reference antibody and/or antibody variants of the disclosure can have a constant region that binds FcγRIIA, FcγRIIB and/or FcγRIIIA with greater affinity than the corresponding wild type constant region.

Thus, anti-TNF-α antibodies of the disclosure can have alterations in biological activity that result in increased or decreased opsonization, phagocytosis, or ADCC. Such alterations are known in the art. For example, modifications in antibodies that reduce ADCC activity are described in U.S. Pat. No. 5,834,597. An exemplary ADCC lowering variant corresponds to "mutant 3" (shown in FIG. 4 of U.S. Pat. No. 5,834,597) in which residue 236 is deleted and residues 234, 235 and 237 (using EU numbering) are substituted with alanines.

In some embodiments, the anti-TNF-α antibodies of the disclosure have low levels of or lack fucose. Antibodies lacking fucose have been correlated with enhanced ADCC activity, especially at low doses of antibody. See Shields et al., 2002, *J. Biol. Chem.* 277:26733-26740; Shinkawa et al., 2003, *J. Biol. Chem.* 278:3466-73. Methods of preparing fucose-less antibodies include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

In yet another aspect, the anti-TNF-α antibodies can be antibodies that have been modified to increase or reduce their binding affinities to the fetal Fc receptor, FcRn, for example, by mutating the immunoglobulin constant region segment at particular regions involved in FcRn interactions (See, e.g., WO 2005/123780). In particular embodiments, a reference antibody and/or antibody variant of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. Such mutations increase the antibody's binding to FcRn, which protects the antibody from degradation and increases its half-life.

In yet other aspects, a reference antibody and/or antibody variant has one or more amino acids inserted into one or more of its hypervariable regions, for example as described in Jung and Plückthun, 1997, *Protein Engineering* 10:9, 959-966; Yazaki et al., 2004, *Protein Eng. Des Sel.* 17(5):481-9. Epub 2004 Aug. 17; and U.S. Pat. App. No. 2007/0280931.

Anti-TNF-α antibodies of the disclosure include antibody conjugates that are modified, e.g., by the covalent attachment of any type of molecule to the antibody, such that covalent attachment does not interfere with binding to TNF-α.

In certain aspects, an anti-TNF-α antibody of the disclosure can be conjugated to an effector moiety or a label. The term "effector moiety" as used herein includes, for example, antineoplastic agents, drugs, toxins, biologically active proteins, for example enzymes, other antibody or antibody fragments, synthetic or naturally occurring polymers, nucleic acids (e.g., DNA and RNA), radionuclides, particularly radioiodide, radioisotopes, chelated metals, nanoparticles and reporter groups such as fluorescent compounds or compounds which can be detected by NMR or ESR spectroscopy.

In one example, anti-TNF-α antibodies can be conjugated to an effector moiety, such as a cytotoxic agent, a radionuclide or drug moiety to modify a given biological response. The effector moiety can be a protein or polypeptide, such as, for example and without limitation, a toxin (such as abrin, ricin A, *Pseudomonas* exotoxin, or Diphtheria toxin), a signaling molecule (such as α-interferon, β-interferon, nerve growth factor, platelet derived growth factor or tissue plasminogen activator), a thrombotic agent or an anti-angiogenic agent (e.g., angiostatin or endostatin) or a biological response modifier such as a cytokine or growth factor (e.g., interleukin-1 (IL-1), interleukin-2 (IL-2), interleukin-6 (IL-6), granulocyte macrophage colony stimulating factor (GM-CSF), granulocyte colony stimulating factor (G-CSF), or nerve growth factor (NGF)).

In another example the effector moieties can be cytotoxins or cytotoxic agents. Examples of cytotoxins and cytotoxic agents include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector moieties also include, but are not limited to, antimetabolites (e.g. methotrexate, 6-mercaptopurine, 6-thioguanine, cytarabine, 5-fluorouracil decarbazine), alkylating agents (e.g., mechlorethamine, thiotepa chlorambucil, melphalan, carmustine (BSNU) and lomustine (CCNU), cyclophosphamide, busulfan, dibromomannitol, streptozotocin, mitomycin C5 and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, anthramycin (AMC), calicheamicins or duocarmycins), and antimitotic agents (e.g., vincristine and vinblastine).

Other effector moieties can include radionuclides such as, but not limited to, $^{111}$In and $^{90}$Y, $^{177}$Lu, Bismuth$^{213}$, Californium$^{252}$, Iridium$^{192}$ and Tungsten$^{188}$/Rhenium$^{188}$ and drugs such as, but not limited to, alkylphosphocholines, topoisomerase I inhibitors, taxoids and suramin.

Techniques for conjugating such effector moieties to antibodies are well known in the art (See, e.g., Hellstrom et al., *Controlled Drug Delivery*, 2nd Ed., at pp. 623-53 (Robinson et al., eds., 1987)); Thorpe et al., 1982, *Immunol. Rev.* 62:119-58 and Dubowchik et al., 1999, *Pharmacology and Therapeutics* 83:67-123).

In certain aspects, an anti-TNF-α antibody is conjugated to a small molecule toxin. In certain exemplary embodiments, an anti-TNF-α antibody of the disclosure is conjugated to a dolastatin or a dolostatin peptidic analogs or derivatives, e.g., an auristatin (U.S. Pat. Nos. 5,635,483 and 5,780,588). The dolastatin or auristatin drug moiety can be attached to the antibody through its N (amino) terminus or the C (carboxyl) terminus (WO 02/088172). Exemplary auristatin embodiments include the N-terminus linked monomethylauristatin drug moieties DE and DF, as disclosed in U.S. Pat. No. 7,498,298, which is hereby incorporated by reference in its entirety (disclosing, e.g., linkers and methods of preparing monomethylvaline compounds such as MMAE and MMAF conjugated to linkers).

In other exemplary embodiments, small molecule toxins include but are not limited to calicheamicin, maytansine (U.S. Pat. No. 5,208,020), trichothene, and CC1065. In one embodiment of the disclosure, the antibody is conjugated to one or more maytansine molecules (e.g., about 1 to about 10 maytansine molecules per antibody molecule). Maytansine can, for example, be converted to May-SS-Me which can be reduced to May-SH3 and reacted with an antibody (Chari et al., 1992, *Cancer Research* 52: 127-131) to generate a maytansinoid-antibody or maytansinoid-Fc fusion conjugate. Structural analogues of calicheamicin that can also be used include but are not limited to $\gamma_1^1$, $\gamma_3^1$, N-acetyl-$\gamma_1^1$, PSAG, and $\theta_1^1$, (Hinman et al., 1993, *Cancer Research* 53:3336-3342; Lode et al., 1998, *Cancer Research* 58:2925-2928; U.S. Pat. No. 5,714,586; U.S. Pat. No. 5,712,374; U.S. Pat. No. 5,264,586; U.S. Pat. No. 5,773,001).

Antibodies of the disclosure can also be conjugated to liposomes for targeted delivery (See, e.g., Park et al., 1997, *Adv. Pharmacol.* 40:399-435; Marty & Schwendener, 2004, *Methods in Molecular Medicine* 109:389-401).

The word "label" when used herein refers to a detectable compound or composition which can be conjugated directly or indirectly to an anti-TNF-α antibody of the disclosure. The label can itself be detectable (e.g., radioisotope labels or fluorescent labels) or, in the case of an enzymatic label, can catalyze chemical alteration of a substrate compound or composition which is detectable. Useful fluorescent moieties include, but are not limited to, fluorescein, fluorescein isothiocyanate, rhodamine, 5-dimethylamine-1-naphthalenesulfonyl chloride, phycoerythrin and the like. Useful enzymatic labels include, but are not limited to, alkaline phosphatase, horseradish peroxidase, glucose oxidase and the like.

6.3. Nucleic Acids and Expression Systems

An anti-TNF-α antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in *Molecular Cloning; A Laboratory Manual*, Second Edition (Sambrook, Fritsch and Maniatis (eds.), Cold Spring Harbor, N.Y., 1989), *Current Protocols in Molecular Biology* (Ausubel, F. M. et al., eds., Greene Publishing Associates, 1989) and in U.S. Pat. No. 4,816,397.

It is possible to express the antibodies of the disclosure in either prokaryotic or eukaryotic host cells. In certain embodiments, expression of antibodies is performed in eukaryotic cells, e.g., mammalian host cells, for optimal secretion of a properly folded and immunologically active antibody. Exemplary mammalian host cells for expressing the recombinant antibodies of the disclosure include Chinese Hamster Ovary (CHO cells) (including DHFR⁻ CHO cells, described in Urlaub and Chasin, 1980, *Proc. Natl. Acad. Sci. USA* 77:4216-4220, used with a DHFR selectable marker, e.g., as described in Kaufman and Sharp, 1982, *Mol. Biol.* 159:601-621), NS0 myeloma cells, COS cells, 293 cells and SP2/0 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown.

Host cells can also be used to produce portions of intact antibodies, such as Fab fragments or scFv molecules. Recombinant DNA technology can also be used to remove some or all of the DNA encoding either or both of the light and heavy chains that is not necessary for binding to TNF-α. The molecules expressed from such truncated DNA molecules are also encompassed by the antibodies of the disclosure.

For recombinant expression of an anti-TNF-α antibody of the disclosure, the host cell can be co-transfected with two expression vectors of the disclosure, the first vector encoding a heavy chain derived polypeptide and the second vector encoding a light chain derived polypeptide. Typically, the two vectors each contain a separate selectable marker. Alternatively, a single vector can be used which encodes both heavy and light chain polypeptides.

Once a nucleic acid encoding one or more portions of D2E7 or of an anti-TNF-α antibody with CDR sequences related to the CDR sequences of D2E7 is generated, further alterations or mutations can be introduced into the coding sequence, for example to generate nucleic acids encoding antibodies with different CDR sequences, antibodies with reduced affinity to the Fc receptor, or antibodies of different subclasses.

Once an anti-TNF-α antibody of the disclosure has been produced by recombinant expression, it can be recovered and purified by any method known in the art for purification of an immunoglobulin molecule, for example, by chromatography (e.g., ion exchange, affinity, particularly by affinity for TNF-α after Protein A or Protein G selection, and sizing column chromatography), centrifugation, differential solubility, or by any other standard technique for the purification of proteins. Further, the anti-TNF-α antibodies of the present disclosure or fragments thereof can be fused to heterologous polypeptide sequences described herein or otherwise known in the art to facilitate purification.

Once isolated, an anti-TNF-α antibody can, if desired, be further purified, e.g., by high performance liquid chromatography (See, e.g., Fisher, *Laboratory Techniques In Biochemistry And Molecular Biology* (Work and Burdon, eds., Elsevier, 1980)), or by gel filtration chromatography on a Superdex™ 75 column (Pharmacia Biotech AB, Uppsala, Sweden).

6.4. Therapeutic Uses

The TNF-α antibodies of the present disclosure are useful for treating disorders or symptoms of various immune and autoimmune pathologies as well as inflammatory diseases.

TNF-α-related pathologies and diseases that can be treated with the anti-TNF-α antibodies of the disclosure include, but are not limited to, the following:

Acute and chronic immune and autoimmune pathologies, such as systemic lupus erythematosus, rheumatoid arthritis, thyroidosis, graft versus host disease, scleroderma, diabetes mellitus, Grave's disease, and the like;

Infections, including, but not limited to, sepsis syndrome, cachexia, circulatory collapse and shock resulting from acute or chronic bacterial infection, acute and chronic parasitic and/or bacterial, viral or fungal infectious diseases, such as AIDS (including sequelae such as cachexia, autoimmune disorders, AIDS dementia complex and infections);

Inflammatory diseases, such as chronic inflammatory pathologies and vascular inflammatory pathologies, including chronic inflammatory pathologies such as sarcoidosis, chronic inflammatory bowel disease, ulcerative colitis, and Crohn's pathology and vascular inflammatory pathologies, such as, but not limited to, disseminated intravascular coagulation, atherosclerosis, and Kawasaki's pathology;

Neurodegenerative diseases, including, but not limited to, demyelinating diseases, such as multiple sclerosis and acute transverse myelitis; extrapyramidal and cerebellar disorders such as lesions of the corticospinal system; disorders of the basal ganglia or cerebellar disorders; hyperkinetic movement disorders such as Huntington's Chorea and senile chorea, drug-induced movement disorders, such as those induced by drugs which block the CNS, dopamine receptors; hypokinetic movement disorders, such as Parkinson's disease; Progressive supranucleo palsy, Cerebellar and Spinocerebellar Disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and Machado-Joseph); and systemic disorders (Refsum's disease, abetalipoprotemia, ataxia, telangiectasia, and mitochondrial multi. system disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type, Wernicke-Korsakoff syndrome; chronic alcoholism; Creutzfeldt-Jakob disease; subacute sclerosing panencephalitis, Hallerrorden-Spatz disease, and Dementia pugilistica, or any subset thereof;

Malignant pathologies involving TNF-α secreting tumors or other malignancies involving TNF-α, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or Mycosis fungoides), and Alcohol-induced hepatitis.

In certain specific embodiments, the antibodies of the disclosure are used to treat any indications for which Adalimumab is approved, e.g., rheumatoid arthritis (RA) (including moderate to severe RA in adults), polyarticular juvenile idiopathic arthritis (JIA) (including moderate to severe JIA in patients 4 years of age and older), psoriatic arthritis (PsA) (including PsA in adults), ankylosing spondylitis (AS) (including AS in adults), Crohn's disease (CD) (including moderate or severe CD in adults), psoriasis, e.g., chronic plaque psoriasis (Ps) (including moderate to severe chronic plaque psoriasis in adults), and axial spondyloarthritis (axSpA) (including severe axSpA in adult patients who have no X-ray evidence of structural damage).

Accordingly, the present disclosure provides methods of treating any of the foregoing diseases in a patient in need thereof, comprising: administering to the patient an anti-TNF-α antibody of the disclosure. Optionally, said administration is repeated, e.g., after one day, two days, three days, five days, one week, two weeks, or one month. The repeated administration can be at the same dose or at a different dose. The administration can be repeated once, twice, three times, four times, five times, six times, seven times, eight times, nine times, ten times, or more. For example, according to certain dosage regimens a patient receives anti-TNF-α therapy for a prolonged period of time, e.g., 6 months, 1 year or more. The amount of anti-TNF-α antibody administered to the patient is in certain embodiments a therapeutically effective amount. As used herein, a "therapeutically effective" amount of TNF-α antibody can be administered as a single dose or over the course of a therapeutic regimen, e.g., over the course of a week, two weeks, three weeks, one month, three months, six months, one year, or longer. A typical dosage will depend on the patient and the severity of the disease, but typically ranges 10 mg and 160 mg (e.g., 10 mg, 15 mg, 20 mg, 25 mg, 30 mg, 35 mg, 40 mg, 45 mg, 50 mg, 60 mg, 80 mg, 100 mg, 120 mg, 140 mg, or 160 mg. In specific embodiments, the disclosure provides a pharmaceutical composition comprising an anti-TNF-α antibody, or a method of treatment of one or more of the disorders disclosed herein, in a dosage range bracketed by any of the foregoing values. The therapeutic regimen in which the anti-TNF-α antibody of the disclosure will vary depending on the patient's age, weight, and disease condition. The therapeutic regimen can continue for 2 weeks to indefinitely. In specific embodiments, the therapeutic regimen is continued for 2 weeks to 6 months, from 3 months to 5 years, from 6 months to 1 or 2 years, from 8 months to 18 months, or the like. The patient to whom an anti-TNF-α antibody of the disclosure is administered is preferably a human. In certain aspects, the human is a pediatric patient. In other aspects, the human is an adult patient.

The anti-TNF-α antibodies of the disclosure can be administered in combination with at least one other therapeutic agent (a "second therapeutic agent"). The anti-TNF-α antibody and the second therapeutic agent can be administered concurrently (either simultaneously or sequentially) or separately.

In certain aspects, the second therapeutic agent is an anti-rheumatic drug, an anti-inflammatory agent, a chemotherapeutic agent, a radiotherapeutic, an immunosuppressive agent, or a cytotoxic drug.

Anti-rheumatic drugs include, but are not limited to, auranofin, azathioprine, chloroquine, D-penicillamine, gold sodium thiomalate hydroxychloroquine, Myocrisin and sulfasalazine methotrexate.

Anti-inflammatory agents include, but are not limited to, dexamethasone, pentasa, mesalazine, asacol, codeine phosphate, benorylate, fenbufen, naprosyn, diclofenac, etodolac and indomethacin, aspirin and ibuprofen.

Chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucovorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrovorum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptopurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, D2E7, tretinoin, valrubicin, vinblastine sulfate, vincristine sulfate, and vinorelbine tartrate.

In yet other aspects of the disclosure, the second therapeutic agent is a TNF-α antagonist other than the anti-TNF-α antibody of the disclosure. Examples of such TNF-α antagonists include, but are not limited to, soluble TNF-α receptors; etanercept (ENBREL; Immunex) or a fragment, derivative or analog thereof; infliximab (REMICADE; Centacor) or a derivative, analog or antigen-binding fragment thereof; IL-10, which is known to block TNF-α production via interferon-γ-activated macrophages (Oswald et al., 1992, *Proc. Natl. Acad. Sci. USA* 89:8676-8680), TNFR-IgG (Ashkenazi et al., 1991, *Proc. Natl. Acad. Sci. USA* 88:10535-10539); the murine product TBP-1 (Serono/Yeda); the vaccine CytoTAb (Protherics); antisense molecule 104838 (ISIS); the peptide RDP-58 (SangStat); thalidomide (Celgene); CDC-801 (Celgene); DPC-333 (Dupont); VX-745 (Vertex); AGIX-4207 (AtheroGenics); ITF-2357 (Italfarmaco); NPI-13021-31 (Nereus); SCIO-469 (Scios); TACE targeter (Immunix/AHP); CLX-120500 (Calyx); Thiazolopyrim (Dynavax); auranofin (Ridaura) (SmithKline Beecham Pharmaceuticals); quinacrine (mepacrine dichlorohydrate); tenidap (Enablex); Melanin (Large Scale Biological); and anti-p38 MAPK agents by Uriach.

Additional second therapeutic agents useful in combination with an anti-TNF-α antibody and particular indications for which combination therapy with such second therapeutic agents are useful are disclosed in WO 2004/004633, which is incorporated by reference herein in its entirety.

6.5. Pharmaceutical Compositions and Pharmaceutical Administration

The anti-TNF-α antibodies of the disclosure can be incorporated into pharmaceutical compositions suitable for administration to a patient. Typically, the pharmaceutical composition comprises an anti-TNF-α antibody and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, and powders. The preferred form depends on the intended mode of administration and therapeutic application. Typical preferred compositions are in the form of injectable or infusible solutions. The preferred mode of administration is parenteral (e.g., intravenous, subcutaneous, intraperitoneal, intramuscular). In a preferred embodiment, the anti-TNF-α antibody is administered by intravenous infusion or injection. In another preferred embodiment, the anti-TNF-α antibody is administered by intramuscular or subcutaneous injection.

The anti-TNF-α antibodies of the disclosure can be provided in pharmaceutical kits. The pharmaceutical kit is a package comprising the anti-TNF-α antibody of the disclosure (e.g., either in lyophilized form or as an aqueous solution) and optionally one or more of the following: a second therapeutic agent, for example as described above; a device for administering the anti-TNF-α antibody, for example a pen, needle and/or syringe; and pharmaceutical grade water or buffer to resuspend the antibody if the antibody is in lyophilized form.

In certain aspects, each unit dose of the anti-TNF-α antibody is packaged separately, and a kit can contain one or more unit doses (e.g., two unit doses, three unit doses, four unit doses, five unit doses, eight unit doses, ten unit doses, or more). In a specific embodiment, the one or more unit doses are each housed in a syringe or pen. A typical unit dose comprises 10 mg to 160 mg of an anti-TNF-α antibody (e.g., 10 mg, 15 mg, 20 mg, 25 mg, 30 mg, 35 mg, 40 mg, 45 mg, 50 mg, 60 mg, 80 mg, 100 mg, 120 mg, 140 mg, or 160 mg). In specific embodiments the present disclosure provides a unit dose comprising an anti-TNF-α antibody in a range bracketed by any of the foregoing values/

In addition, other additives can be included, such as stabilizers, buffers (e.g., a block buffer or lysis buffer), and the like. In a specific embodiment, the antibody and one or more additives can be provided (individually or combined) as dry powders, usually lyophilized, including excipients which on dissolution will provide a solution having the appropriate concentration.

7. EXAMPLES

7.1. Example 1

Vectors for Expression and Cell-Surface Display

Synthetic variable light ($V_L$) and variable heavy ($V_H$) domains for D2E7 (Adalimumab) were constructed by a commercial gene synthesis supplier (DNA 2.0 Inc., Menlo Park, Calif.). FIGS. 1A-1C show the DNA sequences, translated amino acid sequences, flanking restriction sites, and CDRs of the synthetic D2E7 $V_H$ and $V_L$ fragments. Complementarity Determining Regions (CDRs) are indicated by bold underlined text. The synthetic D2E7 $V_H$ and $V_L$ were cloned into vector pYA206, an Epstein-Barr virus derived episomal vector for expression and display of antibodies on the surface of mammalian cells. pYA206 is a derivative of plasmid pYA104 (Akamatsu et al., J. Immunol. Methods, 2007 Oct. 31; 327(1-2):40-52) with the following modifications: 1) the human C lambda constant domain has been replaced with the human C kappa constant domain, 2) the glycosidylphosphatidylinositol linkage signal (GPI anchor) has been replaced with the transmembrane domain of the Platelet Derived Growth Factor receptor (PDGF-R), 3) unique NotI and XhoI sites are upstream of the C kappa domain for cloning $V_L$ domains in frame with C kappa, and 4) unique NgoMIV and SacI sites are upstream of IgG$_1$ for cloning $V_H$ domains in frame with the IgG$_1$ constant regions.

pCW600 is a derivative of plasmid pYA206, with the CH gene replaced with Fab.

The D2E7 $V_H$ fragment was digested with NgoMIV and SacI, and the D2E7 $V_L$ fragment was digested with NotI and XhoI. Both fragments were cloned into plasmid pYA206 to create plasmid pYA206-D2E7. FIG. 4 shows the structure of pYA206-D2E7. This plasmid contains the EBNA-1 gene and oriP from Epstein Barr virus which allows replication in mammalian cells as an episome. The pUC origin of replication and ampicillin resistance gene allow the plasmid to be propagated in *E. coli*. Mammalian cell transformants are selected for with the puromycin resistance gene under control of the SV40 promoter. The CMV promoter and internal ribosome entry site (IRES) allow for expression of the displayed antibody heavy and light chains. The expressed antibody is tethered to the cell membrane via the PDGF-R transmembrane domain fused to the end of the IgG$_1$ constant domain.

The D2E7 V$_H$ fragment was digested with NgoMIV and SacI, the D2E7 V$_L$ fragment was digested with NotI and XhoI, and both fragments were cloned into plasmid pCW600 to create plasmid pCW600-D2E7. FIG. 4 shows the structure of pCW600-D2E7. This plasmid contains the EBNA-1 gene and oriP from Epstein Barr virus which allows replication in mammalian cells as an episome. The pUC origin of replication and ampicillin resistance gene allow the plasmid to be propagated in *E. coli*. Mammalian cell transformants are selected for with the puromycin resistance gene under control of the SV40 promoter. The CMV promoter and internal ribosome entry site (IRES) allow for expression of the displayed Fab heavy and light chains. The expressed Fab is tethered to the cell membrane via the PDGF-R transmembrane domain fused to the end of the IgG$_1$ constant domain.

7.2. Example 2

Surface Display and FACS Titration Assay of D2E7

293c18 cells (American Type Culture Collection, Manassas, Va.), which express the EBNA-1 protein, were transformed with pYA206-D2E7. 293c18 cells were cultured in DMEM media supplemented with 10% Fetal Bovine Serum (FBS) and 0.25 mg/ml G418. 0.125 µg pYA206-D2E7 or pCW600-D2E7 plasmid was mixed 1:200 with 25 µg pUC 19 as a carrier plasmid plus 60 µl lipofectamine (Invitrogen, CA) and added to 2×10$^7$ 293c18 cells. The 200 fold excess carrier plasmid was to ensure that each cell was transformed by at most a single D2E7 containing plasmid. After 48 hours, transformed cells were selected by addition of puromycin, and then cultured for an additional 18 days before FACS analysis.

Figure 5:
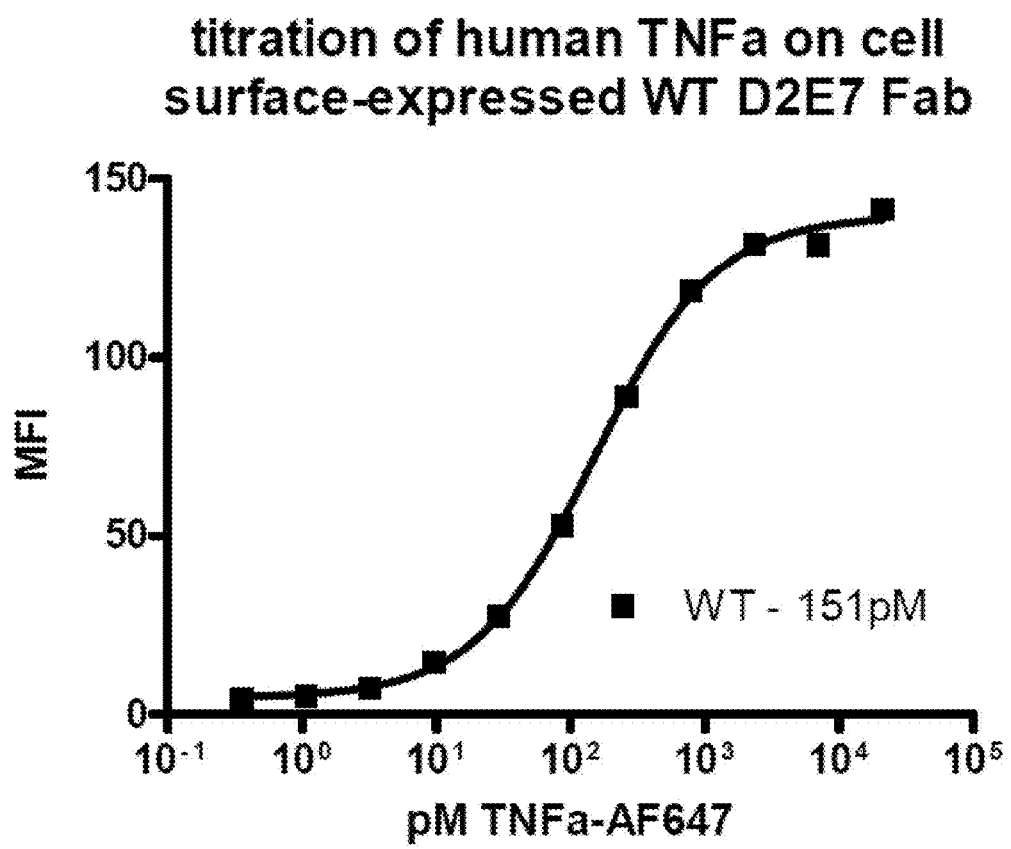

Human TNF-α (R&D Systems, Minneapolis, Minn.) was labeled with Alexa Fluor 647 (Invitrogen, CA). 1 mg human TNF-α was reacted with 84 ug Alexa Flour 647 reagent for 30 minutes at room temperature, and then purified from unreacted reagent using a gel filtration column. 293c18 cells transfected with pCW600-D2E7 were doubly stained with PE-labeled anti-human IgG (Southern Biotech) at 1/200 dilution and various concentrations of Alexa Fluor 647-labeled TNF-α on ice for one hour, washed with FACS buffer (phosphate buffered saline (PBS) plus 0.5% Bovine Serum Albumin (BSA)) and analyzed on a FacsCalibur (BD). A titration curve was performed with concentrations of Alexa Fluor 647-labeled TNF-α ranging from 20 nM to 0.26 nM. The midpoint of each curve, at which half maximal binding occurs, defined EC$_{50}$ for the antibody/antigen complex. Results for wild type D2E7 are shown in FIG. 5. Surface displayed D2E7 Fab binds to TNF-α with an EC$_{50}$ of 0.15 nM in this assay.

Figure 6:
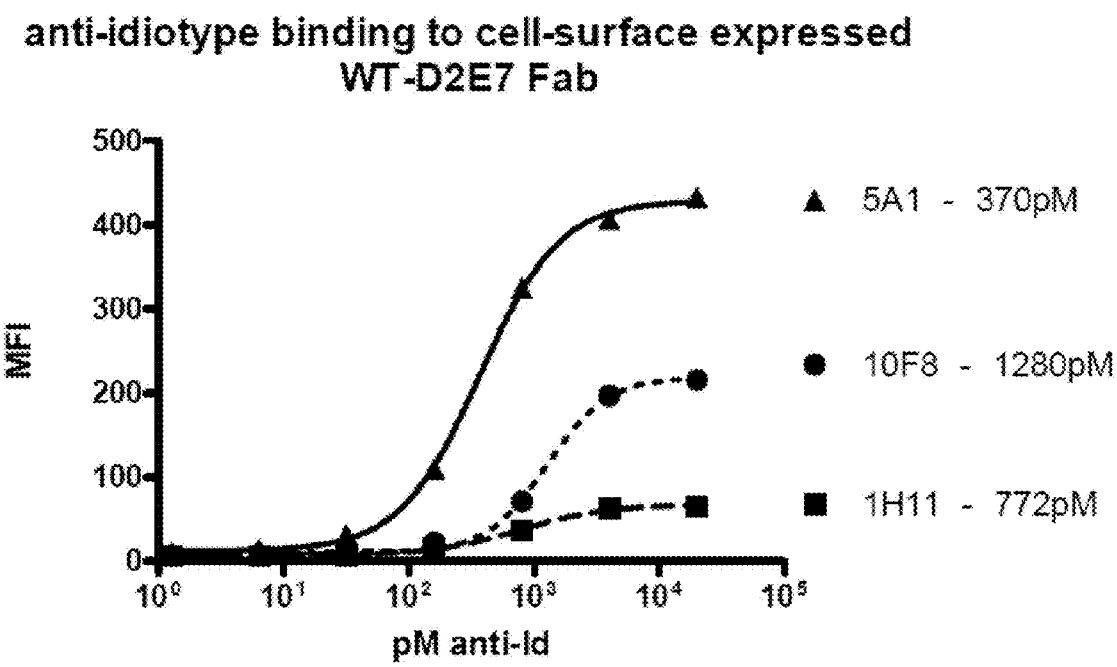

Anti-D2E7 antibodies 1H11, 5A1, and 10F8 (anti-idiotypes, anti-Ids) were conjugated with biotin. 1 mg of each anti-Id was reacted with 43 µg Sulfo-NHS-LC-biotin (Pierce) reagent for two hours at room temperature. Excess biotin was removed by spinning in an Amicon microcentrifuge filter. 293c18 cells transfected with pCW600-D2E7 were doubly stained with PE-labeled anti-human IgG (Southern Biotech) at 1/200 dilution and biotinylated anti-Ids for 1 hour, washed with FACS buffer (phosphate buffered saline (PBS) plus 0.5% Bovine Serum Albumin (BSA)), then stained with 1/200 dilution of streptavidin-APC. A titration curve was performed with concentrations of anti-Ids ranging from 20 nM to 0.26 nM. The midpoint of each curve, at which half maximal binding occurs, is defined EC$_{50}$ for the anti-Id/D2E7 complex. The result for each anti-idiotype is shown in FIG. 6. Surface displayed D2E7 Fab binds to anti-Ids 1H11, 5A1, and 10F8 with an EC$_{50}$ of 0.77 nM, 0.37 nM, and 1.28 nM, respectively, in this assay.

7.3. Example 3

Construction of Libraries of D2E7 Single Amino Acid Mutants

Each D2E7 CDR amino acid position (underlined in FIG. 1A)—a total of 34 V$_H$ positions and 27 V$_L$ positions—were targeted for NNK randomization. The NNK coding scheme was used (in which N=A, C, G, or T and K=G or T) because 1) only 32 codons are required to encode all 20 naturally occurring amino acids, 2) only a single stop codon (TAG) is included in the 32, and 3) the maximum degeneracy (number of different codons encoding a single amino acid) is 3, rather than the maximum 6-fold degeneracy that occurs in the complete 64 codon genetic code.

61 different DNA fragments, each with NNK degeneracy at a different CDR position, were synthesized by a commercial supplier of synthetic genes (DNA 2.0, Menlo Park, Calif.). These fragments were PCR amplified with primers D2E7reampFwd (5'-CTCGAAAATAATAAAGGGAAAAT-CAG-3') (SEQ ID NO:11) and D2E7reampRev (5'-TGG-TAGTGTGGGGACTC-3') (SEQ ID NO:12). PCR products were purified, then V$_H$ fragments were digested with Ngo-MIV and SacI, and V$_L$ fragments were digested with NotI and XhoI. All fragments were run on an agarose gel, purified, and subcloned into plasmid pCW600-D2E7 carrying the opposite wild-type variable region fragment. The resulting plasmids were separately transformed into *E. coli* Top 10 cells (Invitrogen, CA) to form a sub-library of transformants for each of the 61 different DNA fragments. The transformations were performed such that at least 10 times more *E. coli* transformants were obtained than the total number of possible codons in each sub-library. The resulting sub-libraries for V$_H$ and V$_L$ were pooled to create two final libraries—a D2E7 V$_H$ library comprising 34 positions and 1088 different codons, and a D2E7 V$_L$ library comprising 27 positions and 864 total different codons.

7.4. Example 4

Figure 7A:
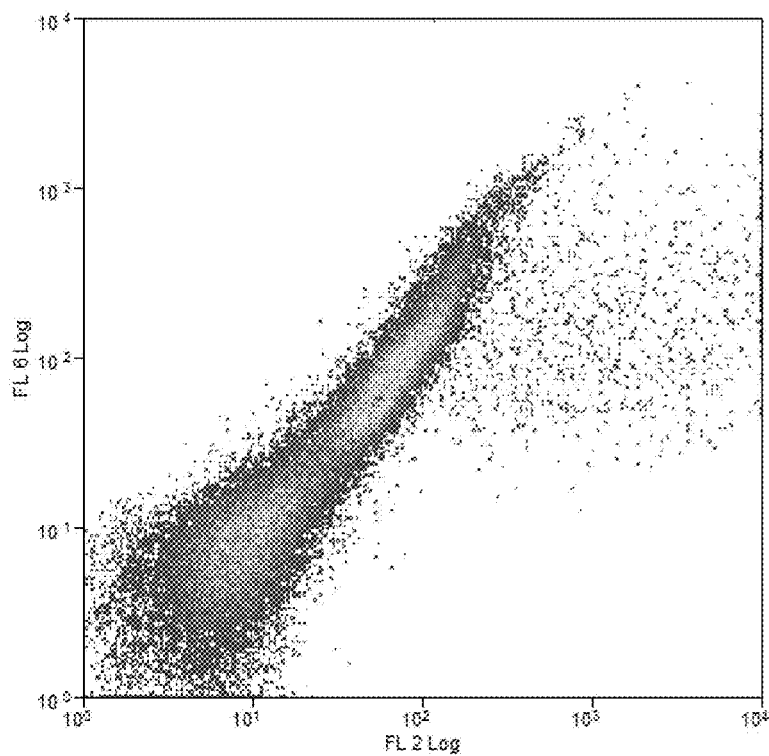
Figure 7B:
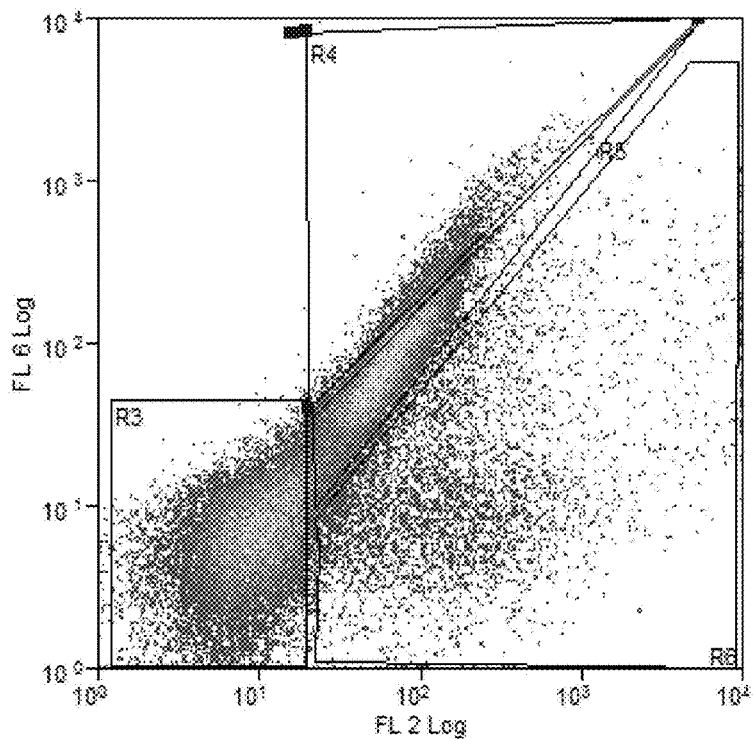

FACS Staining and 4-Way Sorting of D2E7 V$_H$ and V$_L$ Point Mutant Fab Libraries for TNF-α Binding D2E7 V$_H$ and V$_L$ libraries were transfected into 293c18 cells with 0.5 µg library plasmid, 100 µg pUC19 carrier plasmid and 250 µl lipofectamine, selected with 0.8 µg/ml puromycin after 2 days, and cultured for an additional 18 days prior to FACS sorting. Cells were stained with 0.15 nanomolar Alexa Fluor 647-TNF-α and 1:200 PE-labeled anti-IgG (Southern Biotech) and sorted on a MoFlo FACS machine (Dako North America Inc., Carpinteria, Calif.). FACS sorting profiles for wild-type D2E7 and the V$_H$ point mutation libraries are shown in FIGS. 7A-7B. Panel A shows the FACS profile for cells transformed with wild-type D2E7 Fab expression plasmid pCW600; the x-axis shows staining with PE-anti-IgG and the y-axis shows staining with Alexa Fluor 647-TNF-α. Because antibody expression is heterogeneous in the cell population, the FACS profile shows individual data points roughly arranged along a diagonal line pointing toward the upper right quadrant.

TNF-α-stained cells of the V$_H$ point mutation library were sorted into 4 subpopulations based on FACS gates (FIGS. 7A-7B, panel B). The behavior of the wild-type antibody under similar FACS conditions was used to set gates to sort the cells in a higher affinity (H) population (R4), a neutral or 'medium' affinity (M) population (R5), a lower affinity (L) population (R6), and a IgG non-expressing (Z) population (R3). The x-axis shows anti-IgG-PE staining and the y-axis shows staining with human-TNF-α-AF647.

7.5. Example 5

Figure 8A:
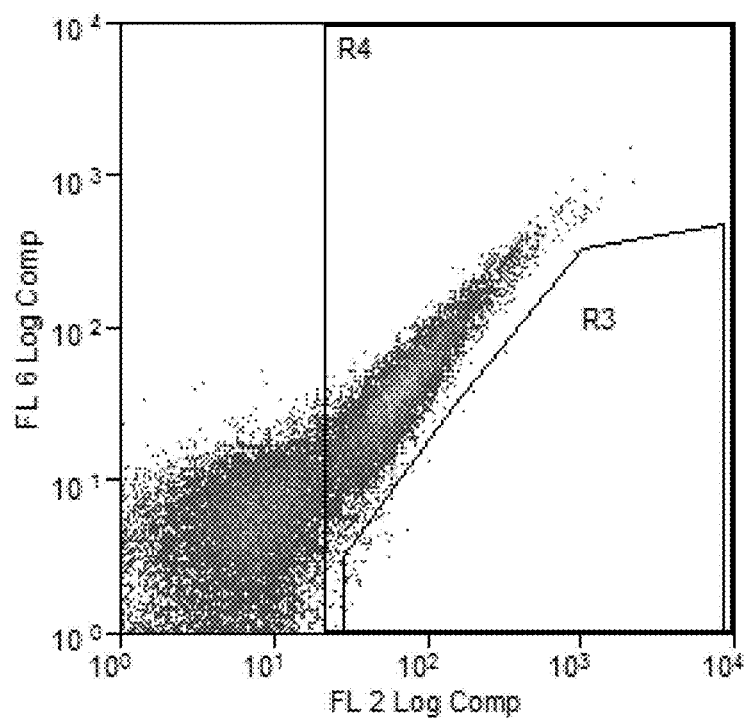
Figure 8B:
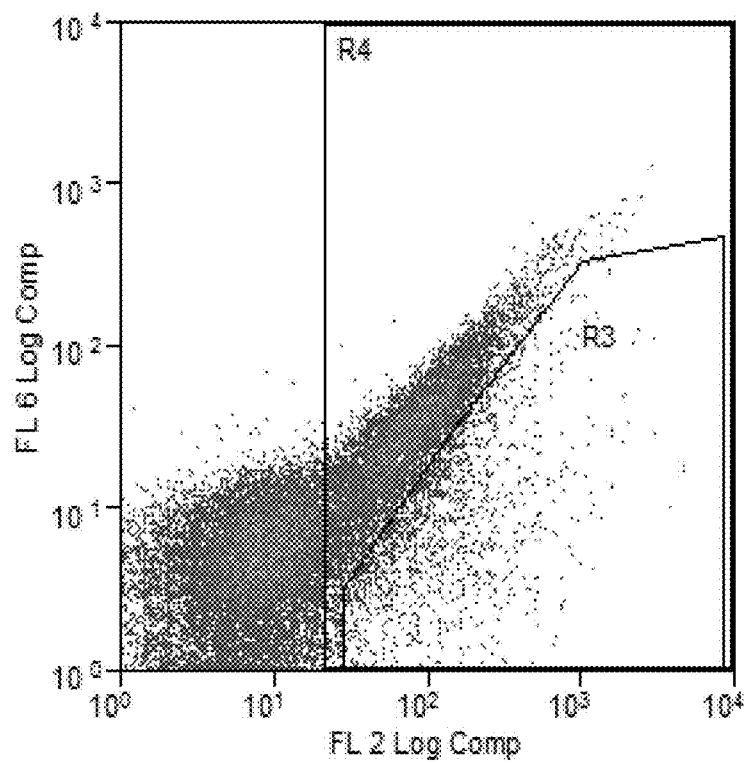

FACS Staining and 2-Way Sorting of D2E7 $V_H$ and $V_L$ Point Mutant Fab Libraries for Anti-Id Binding Cells expressing D2E7 were co-stained with 0.15 nanomolar Alexa Fluor 647-TNF-α and biotinylated anti-idiotype mAbs at $EC_{50}$ (1H11 at 0.77 nM, 5A1 at 0.37 nM, and 10F8 at 1.28 nM), then incubated for two hours at room temperature. Cells were then washed and incubated with streptavidin-APC and anti-human IgG kappa-FITC for one hour at 4° C. Cells were washed, then sorted on a MoFlo FACS machine (Dako North America Inc., Carpinteria, Calif.). FACS sorting profiles for wild-type D2E7 and $V_H$ library stained with 1H11 are shown in FIGS. 8A-8B. Anti-IgG-PE staining is shown on the x-axis and anti-Id1H11-APC staining is shown on the y-axis. A 2-way sort was performed, collecting a minimum of two million cells in the "sorted" (cells with low binding to the anti-idiotype) and "expression" (cells positive for anti-human IgG Kappa FITC) gates.

Because antibody expression is heterogeneous in the cell population, the FACS profile shows individual data points roughly arranged along a diagonal line pointing toward the upper right quadrant. FACS profiles for D2E7 WT and VH point mutation library are shown in FIG. 8, panels A and B, respectively. In order to collect a reference cell population for each library that contains all the expressed point mutations in their correct frequencies in the library, gates were drawn with the left edge parallel to the y-axis; sorting with these gates collects all cells expressing IgG beyond a certain level, regardless of how well the displayed antibodies bind to anti-Id. These were designated the "expression gates" and "expressed populations" (panel B "R4"). Other sortings were done with the top of the gate drawn roughly parallel to and directly below the main diagonal of the wild-type population; these gates were designed to collect cells that expressed antibodies with decreased binding affinity for anti-idiotype, regardless of their overall level of IgG expression. These gates and populations were referred to as the "sort gates" and "sorted populations" (panel B "R3"). Approximately 2,000,000 cells were collected in both the "sorted" and "expression" gate.

7.6. Example 6

Massively Parallel Sequencing of the "Expressed" and "Sorted" Populations

Plasmids were recovered from the "expressed" and "sorted" cell populations and PCR amplification performed to prepare short amplicons suitable for massively parallel sequencing. PCR primers were used which anneal immediately outside of the CDR1 and CDR3 regions of the D2E7 $V_H$ and $V_L$ domain. The primers were: $V_H$ forward primer D2E7_VH_CDR1_for 5'-TTAGTTGTGCTGCATCAG-GTTT-3' (SEQ ID NO:13); $V_H$ reverse primer D2E7_VH_CDR3_rev 5'-GGTCACCAGTGTTCCCTGAC-3' (SEQ ID NO:14); $V_L$ forward primer D2E7_VL_CDR1_for 5'-GTAGGCGACAGGGTCACAAT-3' (SEQ ID NO:15); and $V_L$ reverse primer D2E7_VL_CDR3_rev 5'-AGTCCGTTTGATCTCGAC-CTT-3' (SEQ ID NO:16). Thus, each amplicon contained complete CDR 1, CDR2, and CDR3 regions for locating and tabulating all point mutations, but omitted much of frameworks 1 and 4. D2E7 $V_H$ and $V_L$ library "sorted" and "expressed" amplicons were then sequenced using the Genome Sequencer FLX as directed by manufacturer. (454 Life Sciences, Branford, Conn.).

A computer program was used to examine the sequences and tabulate the number of times each point mutation was found in the "expressed" and "sorted" populations. The computer program initially reads out and tabulates each codon. For amino acids with more than one codon, the program adds the occurrence of the different codons for each amino acid together to make an overall summary of the behavior of that amino acid variant in each subpopulation.

For the 4-way sort of the D2E7 libraries to assess binding to TNF-α, an Enrichment Ratio (ER) score is given for each codon variant. The ER denotes how much more or less frequent the variant is found in the H population compared to its overall frequency. Similarly, Enrichment Ratios can be calculated for each variant in each of the M, L, and Z populations. Higher affinity variants are expected to be enriched in the H population (ER>1) and depleted (ER<1) in the L population. Conversely, lower affinity mutants are expected to be depleted in the H population (ER<1) and enriched in the L population (ER>1). It is possible to identify higher, lower, and neutral affinity variants merely by looking at Enrichment Ratios for the H population.

In the 2-way FACS analysis to assess binding of D2E7 libraries to anti-idiotypes, the "sorted" population contains variants that binds lower to the anti-idiotype. In this case, a higher ER of sorted variants denotes a decreased binding to the anti-idiotype.

7.7. Example 7

Identification of Point Mutants with Desired Properties

To analyze the data, the number of times a mutation is found at a given position is normalized for the number of times that position is sequenced and expressed as a frequency per 1000 sequences. Then the frequency of the mutation in the sorted population is divided by the frequency in the expressed population to give the Enrichment Ratio (ER) which indicates whether the mutation has been enriched or depleted in the sorted population compared to the expressed population, and to what extent. Mutations that are enriched in the sorted population will have enhanced binding to TNF-α, while mutations that are depleted will have decreased binding. Similarly, sorted cells that had decreased binding to anti-idiotypes will have a high Enrichment Ratio for that particular anti-idiotype.

7.8. Example 8

Silent Wild Type Codon Analysis

In determining whether variants in a library have been enriched or depleted in a sorted subpopulation it is useful to compare the behavior of the variants to the behavior of the wild-type protein under the same experimental conditions. This can readily be done by following the behavior of silent WT codons-variant DNA sequences which encode a WT protein but which contain a silent codon change resulting from NNK randomization. For example, at a library position where the wild-type codon is GGG (glycine), NNK randomization will produce a GGT codon, also encoding glycine, but which can be followed in the sorting and statistical analysis processes described herein like any other variant. Depending on the starting codon, anywhere from zero to three silent wild-type codons can occur at any position; in practice this ensures that several dozen silent wild-type codons will be available in a typical CDR library covering 50-65 different positions. The average of these silent wild-type enrichment ratios can be used to determine the midpoint of an experiment; improved affinity variants will be found above this midpoint, lower affinity variants will be found below this midpoint, and neutral variants will be found in the vicinity of the midpoint. FIG. 9 shows the results of a silent wild type codon analysis. Beneficial mutations (i.e. those with decreased binding to anti-idiotype 1H11 and neutral binding to TNF-α) would have a 1H11-ER higher than 0.25 (avg+ 1SD) and a TNF-α-ER between 1.21 and 1.59 (avg+/−1SD).

7.9. Example 9

One-Point FACS Analysis

Figure 11:
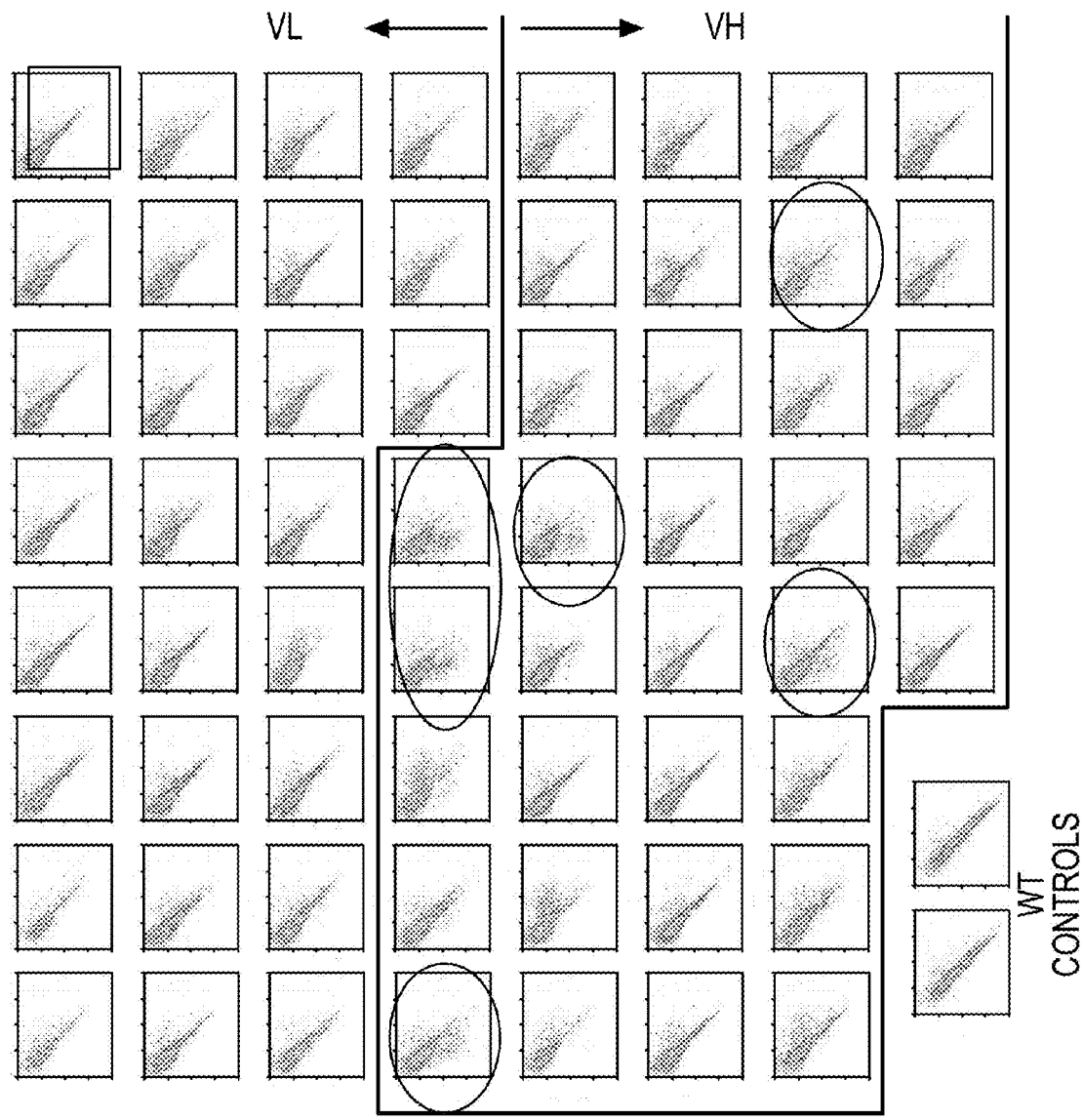
Figure 12:
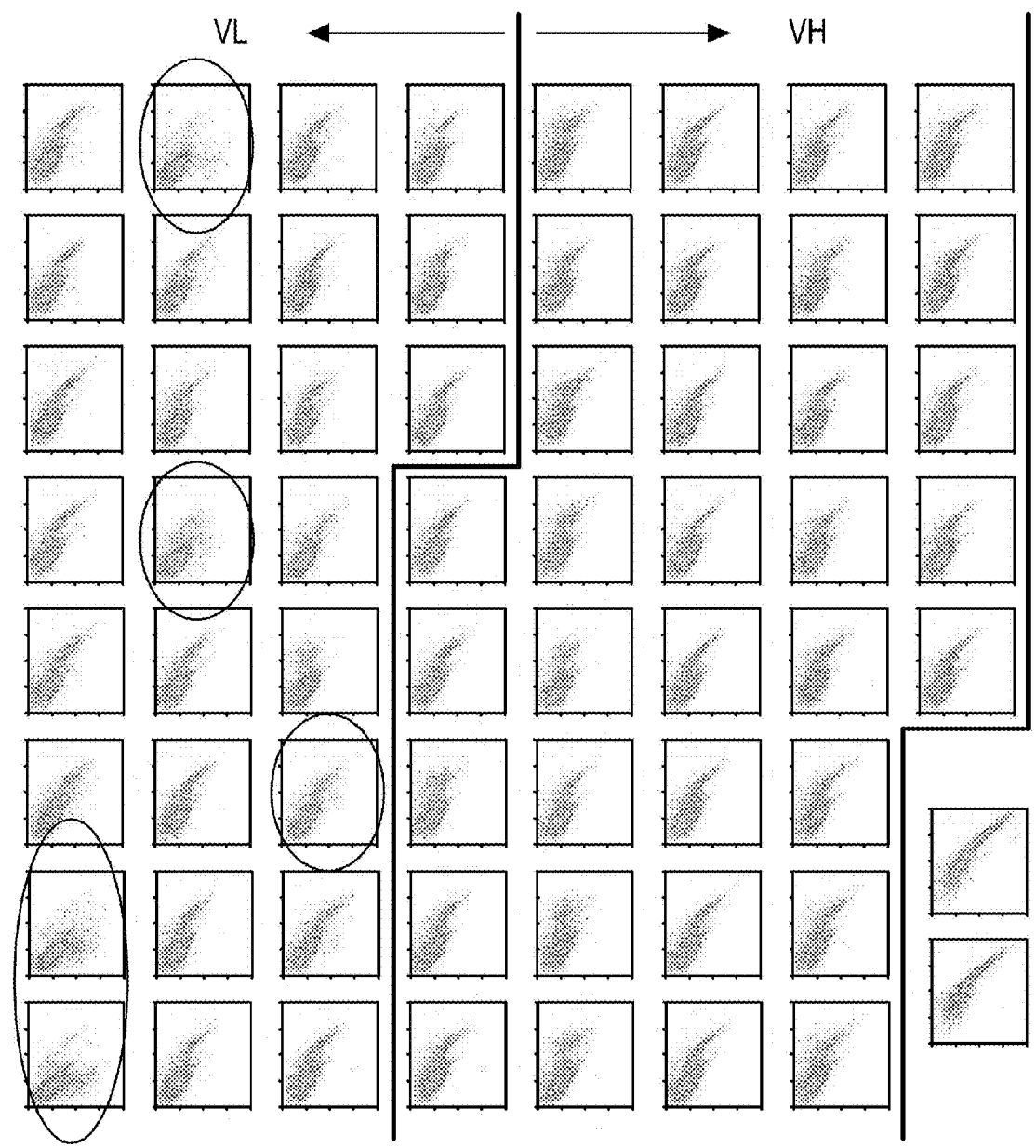

To predict positions in CDR that would lead to decreased binding to anti-idiotypes, 293c18 cells plated in 96-well plates were transfected with sub-libraries with only one position mutated to 32 possible codons (FIG. 10). After two days in culture, cells were harvested and stained with anti-idiotypes at $EC_{50}$ conjugated to PE and TNF-α-647 at $EC_{50}$. FACS analysis showed positions with a large population of cells with low binding to anti-idiotype. FIG. 11 shows that some positions (circled) in $V_H$ can be mutated to decrease 1H11 binding and that no $V_L$ positions can lead to a similar effect. Similarly, FIG. 12 shows that binding by anti-idiotypes 5A1 and 10F8 can be decreased by mutations in certain positions in the $V_L$ chain. Mutations in the $V_H$ chain do not decrease binding to 5A1 and 10F8.

A Pymol model of the of D2E7 with the positions in $V_H$ predicted to be important for 1H11 binding grayed out is shown in FIGS. 13A-13D. The predicted epitope shows that although the positions are scattered between the three CDRs, they are adjacent in the model and form a conformational and discontinuous epitope. Similarly, FIGS. 14A-14D show that the positions in $V_L$ important in 5A1 and 10F8 binding form a conformation or discontinuous epitope.

To confirm decreased binding to anti-idiotype, single mutant full-length IgG is expressed on cell surface, then stained with anti-idiotype conjugated to AF647 at $EC_{50}$ and anti-IgG-PE. To confirm neutral binding to target, full-length IgG on cell surface is stained with TNF-α-AF647 at $EC_{50}$ and anti-IgG-PE.

Figure 15:
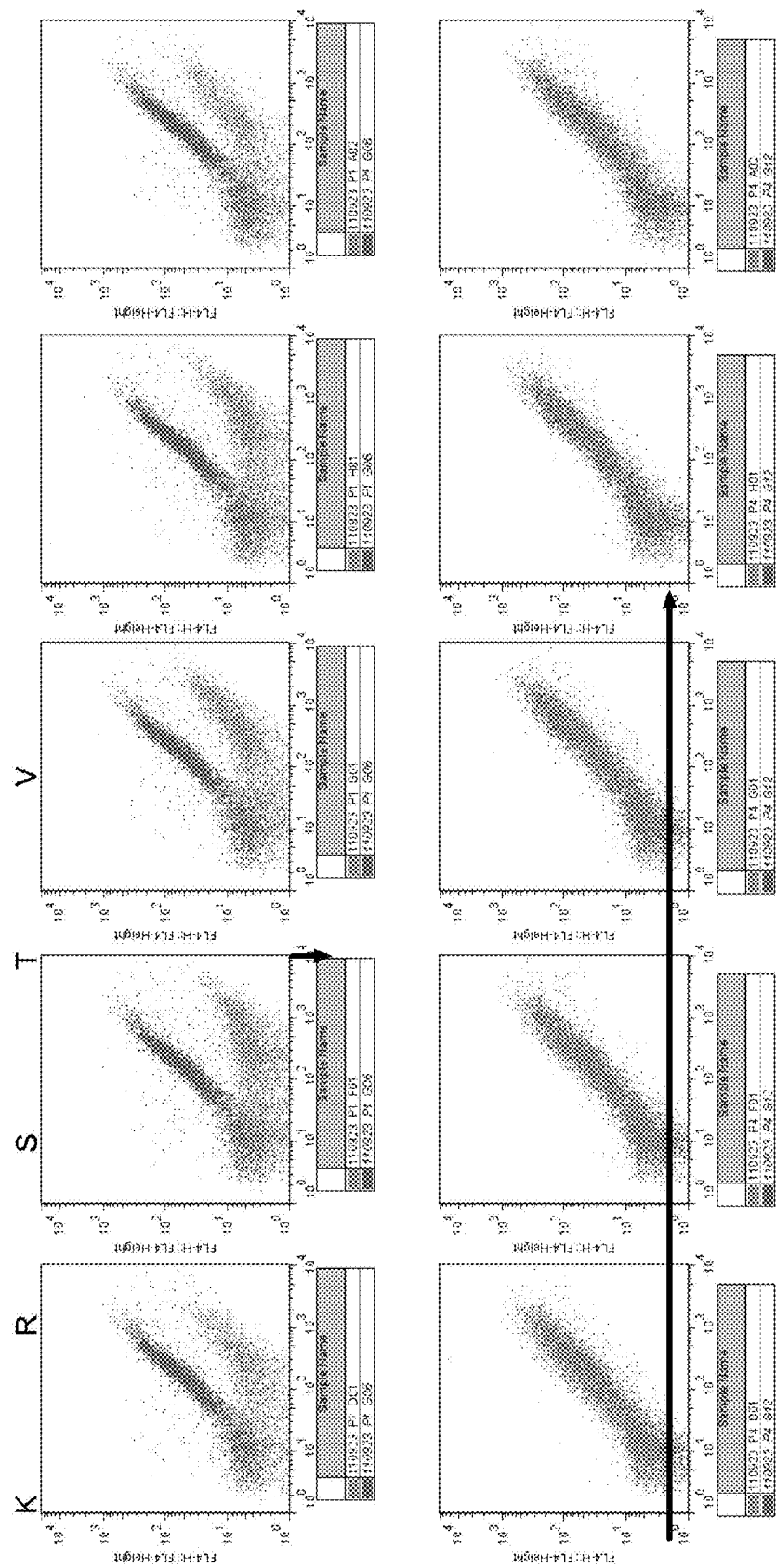

$V_H$ CDR1-2 (Y32) was mutated from Y to K, R, S, T, or V. FIG. 15 shows one-point FACS analysis of the mutants. FACS staining with the anti-idiotype 1H11 confirms decreased binding of all the variants. TNF-α staining shows neutral binding for all mutants except for T, correlating with the lower ER of this mutant in FIG. 16. Beneficial mutations in D2E7 $V_L$, shown in FIG. 16, were selected as ones with a decreased binding to 1H11 (1H11-ER higher than 0.25) and a neutral binding to TNF-α (TNF-α-ER of 1.21-1.60). In grey are unwanted mutations.

Figure 17:
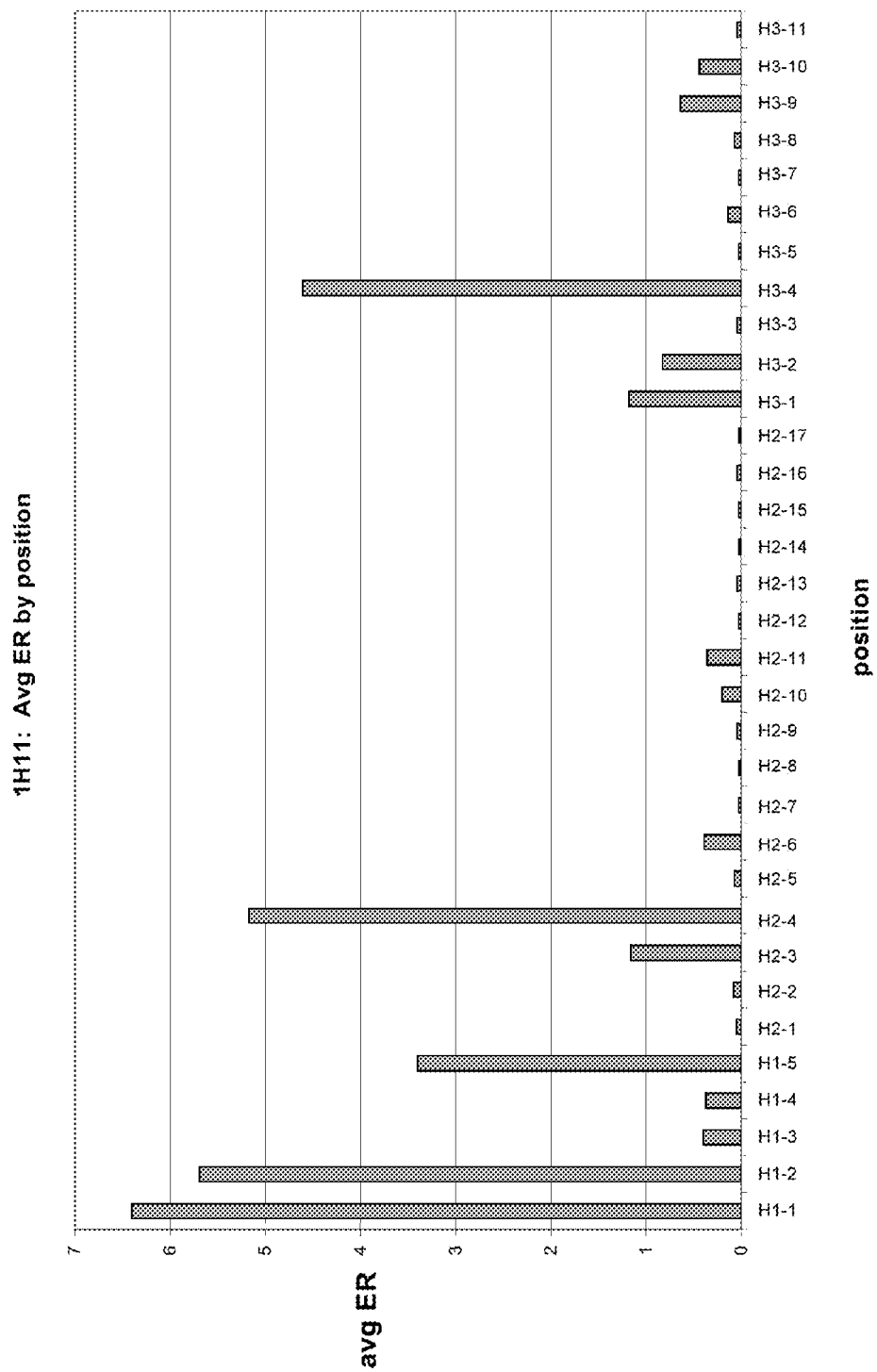

FIG. 17 provides average 1H11 Enrichment Ratios by position. Positions in D2E7 $V_H$ with a high average ER have more possible amino acid substitutions leading to an antibody with decreased binding to anti-Id 1H11.

Figure 18:
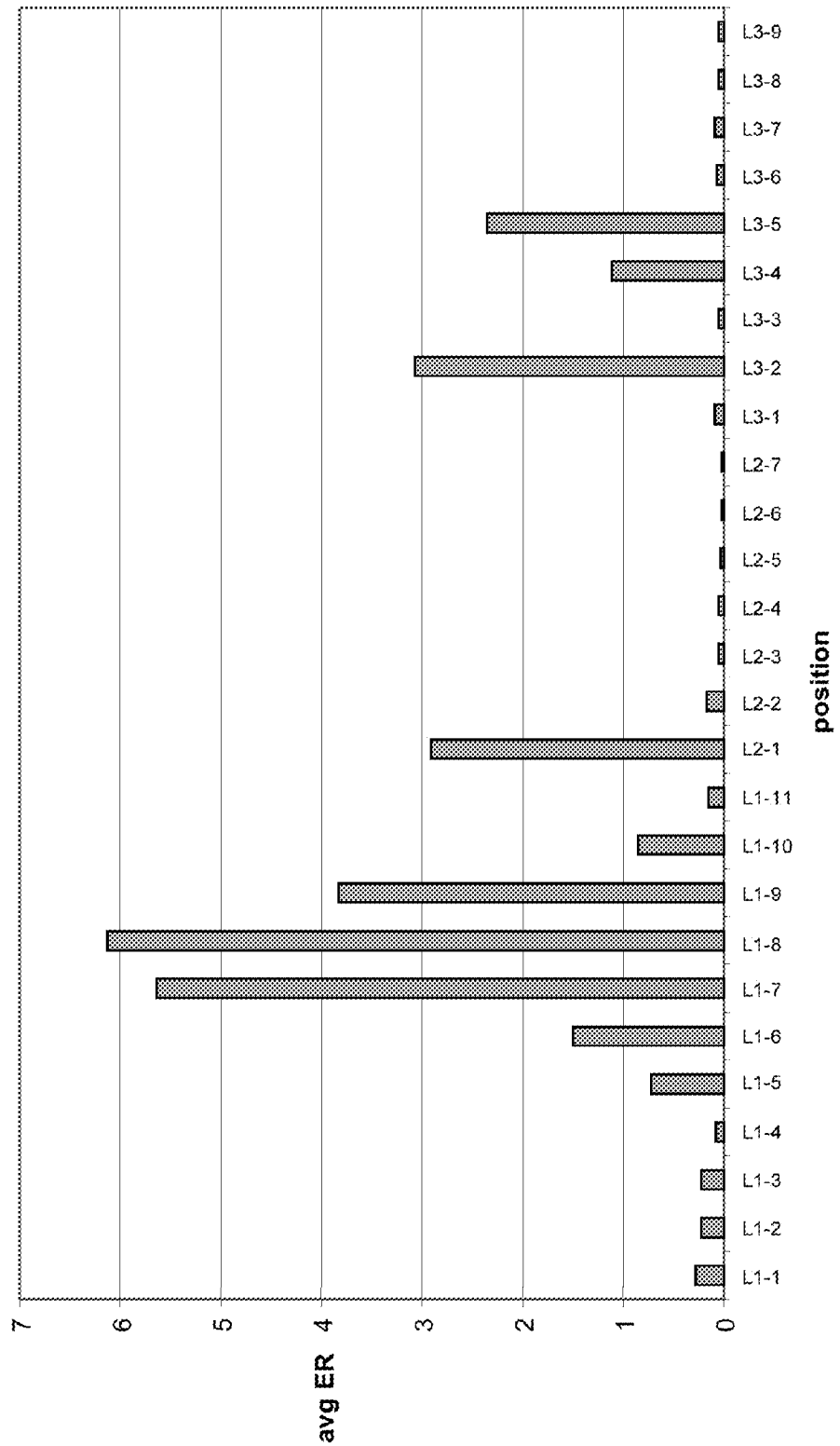

FIG. 18 provides average 5A1 Enrichment Ratios by position. Positions in D2E7 $V_L$ with a high average ER have more possible amino acid substitutions leading to an antibody with decreased binding to anti-idiotype 5A1.

Figure 19:
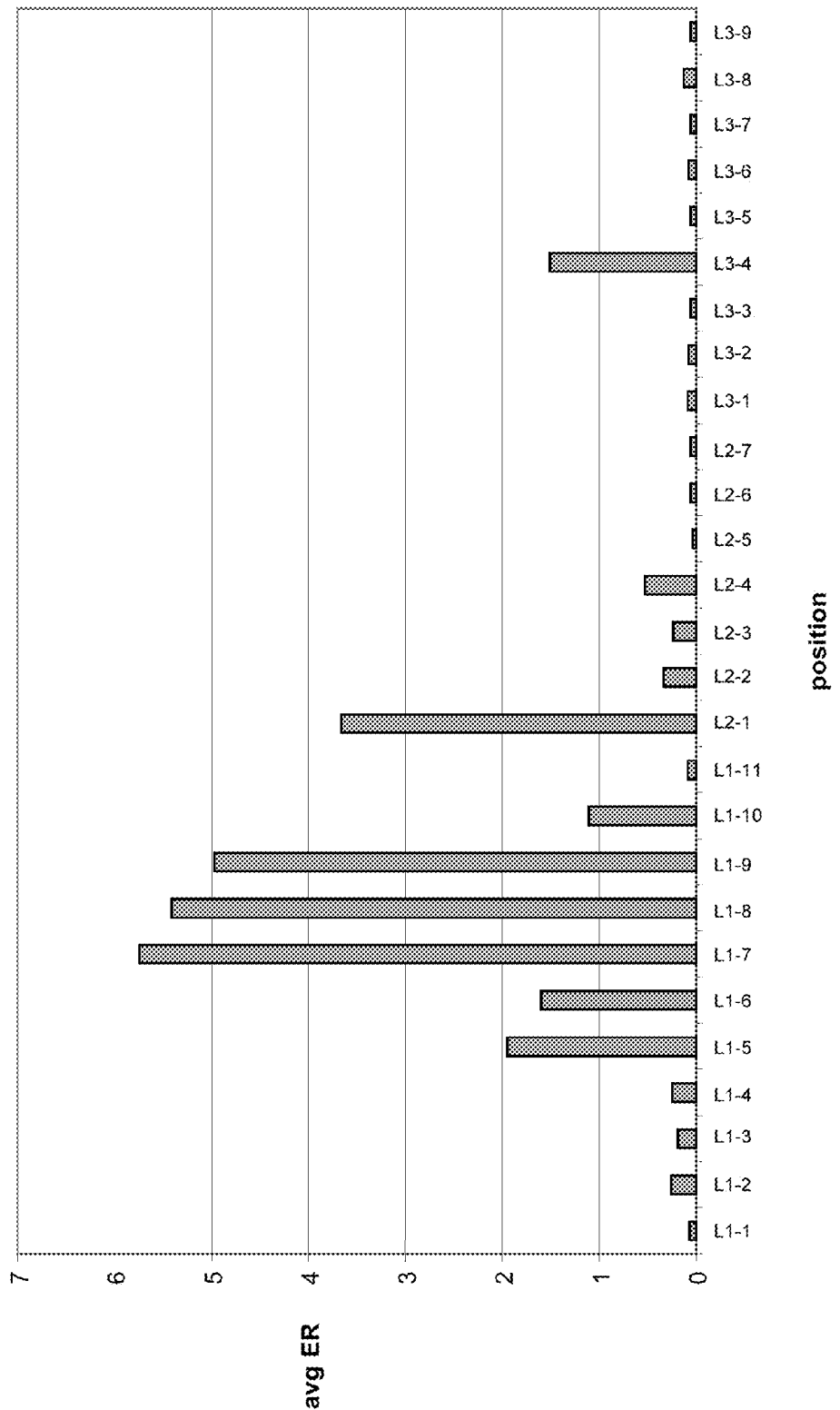

FIG. 19 provides average 10F8 Enrichment Ratios by position. Positions in D2E7 $V_L$ with a high average ER have more possible amino acid substitutions leading to an antibody with decreased binding to anti-idiotype 10F8.

7.10. Example 10

D2E7 Bridging Assay

A D2E7 bridging assay was developed to visualize binding of D2E7 to anti-Adalimumab antibodies (ADAb) obtained from human donors. Immobilon high-binding ELISA plates were coated with 0.5 μg/ml wild-type D2E7 antibody in PBMS at 4° C. overnight. The next day the plates were washed with PBS containing 0.1% Tween-20 (PBS/Tween). The plates were blocked with 1% human AB serum in PBS (huAB/PBS) at room temperature for 1-2 hours. Human serum samples (Bioreclamation, NY) were diluted in huAB/PBS and added to the ELISA plates. Finally, biotinylated wild-type D2E7 antibody was added to a final concentration of 15 ng/ml. Plates were incubated at 4° C. overnight. The next day, plates were washed in PBS/Tween. Streptavidin-HRPO (MABTECH) was diluted 1:1000 as per manufacturer's recommendation in huAB/PBS and 100 μl/well was added to the plates. The plates were incubated for 30 minutes at room temperature then washed once with PBS/Tween and twice with distilled water. TMB One Component (BioFX Laboratories) was added and the color developed for 15 minutes. Plates were read at 650 nm. A positive control was included (murine anti-human D2E7 monoclonal antibody).

7.11. Example 11

Inhibition Assay to Validate D2E7 $V_H$ and $V_L$ Point Mutants

Commercially available serum samples from human donors listing Adalimumab, but not methotrexate, as a medication on their consent forms were screened for the presence of anti-Adalimumab ("ADAb") using the bridging assay of Example 10. Donors who showed evidence of ADAb were selected for further study. The specificity of the ADAb was confirmed by performing inhibition assays using the positive and negative controls described below. The selected donors' ADAb was specific for the Fab fragment of D2E7.

Variant antibodies identified as having reduced binding to murine anti-idiotype antibodies as compared to D2E7 were screened for inhibition of the D2E7 bridging assay. Inhibition of the bridging assay by a variant antibody shows that the variant is still capable of being bound by patient serum ADAbs. Therefore, variants that do not interfere with the bridging assay do not cross-react with the ADAb and therefore represent mutations within the antibody-binding epitope of D2E7.

Immobilon ELISA plates were coated overnight with 0.5 μg/ml wild-type D2E7, washed and blocked. In a separate 96 well plate, D2E7 variant antibodies were diluted in huAb/PBS to 10 μg/ml. Each variant was tested in duplicate. Herceptin and DP10, $IgG_1$ antibodies unrelated to D2E7, were used as negative controls for anti-Adalimumab antibody binding. Wild-type D2E7 antibody was used as a positive control for inhibition. DP10 and D2E7 Fab fragments were also used as negative and positive controls, respectively. Serum from donors exhibiting an immune response to Adalimumab was diluted to 1:25 in huAB/PBS, and 100 μl was added to the wells containing the variants and controls. The final concentration of donor serum was 1:50. 100 μl of the diluted serum with added variants and controls was transferred to the D2E7 coated plates. 100 μl of biotinylated D2E7 at 30 ng/ml in huAB/PBS was immediately added to the plates. The plates were incubated at 4° C. overnight. The next day the plates were washed, and diluted streptavidin-HRPO was added. Plates were washed once with PBS/Tween-40, and TMB One Component (BioFX Laboratories) was added and the color developed for 15 minutes. Plates were read at 650 nm.

Figures 21A, 21B:
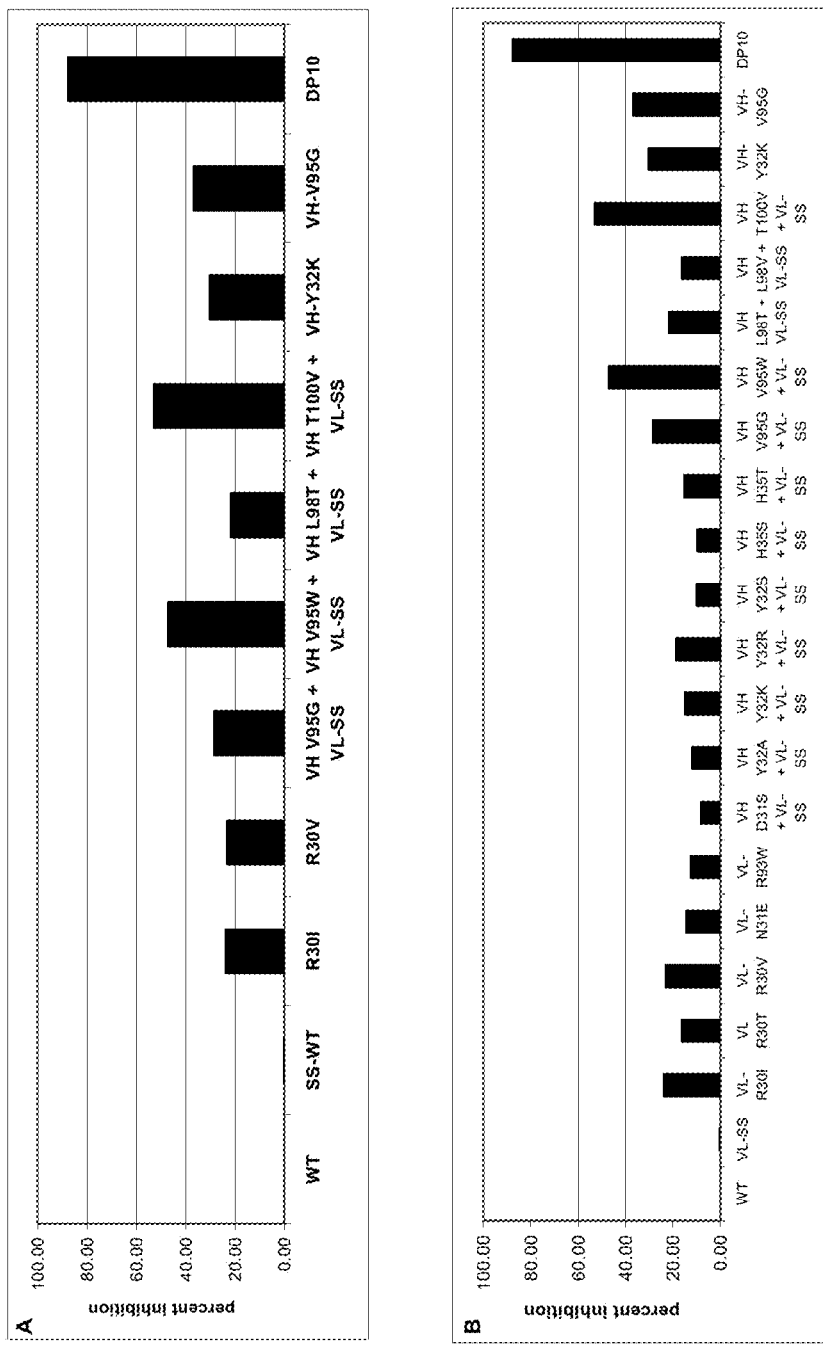
FIGS. 21A-21B show anti-TNF-α variant antibodies with the greatest reductions in binding to anti-Adalimumab antibodies. VL-SS refers to a VL having the substitutions G28S and A34S in CDR-L1 (Kabat numbering), corresponding to the G5S+A11S combination in CDR-L1.

The unrelated antibody DP10 was included as a control in all tests and had no impact on ADAb binding to D2E7 on the plates. The percent inhibition of ADAb binding to DP10 averaged 88+/−12%. The inhibition assay was performed with ADAb positive serum samples from four commercial donors. The results largely overlapped for all four donors, with changes to the $V_H$ CDR3 having the largest impact on ADAb binding (FIGS. 20A-20B). Preferred variants were selected in two ways: FIG. 21A shows a list of all the variants that had percent inhibition greater than 2 standard deviations above the average for all the variants tested. FIG. 21B shows all the variants that had any significant activity in any of the four donors. The best point mutation identified was T100V with a percent inhibition of 53+/−10%. The second best was V95W with an average of 47%. The best variant outside of the $V_H$ CDR3 was $V_L$ R30 with two variant amino acid substitutions with an average percentage of 23%.

Combination variants were created based on the data for single variants. Combinations that contained changes in both the VH and the VL were constructed, in some cases incorporating the substitutions into a variant VL having the substitutions G28S and A34S in CDR-L1 (Kabat numbering), corresponding to the G5S+A11S combination in CDR-L1 as initially described in WO 2010/121140. The variant VL backbone with the G5S+A11S substitutions is referred to herein as VL-SS. The variant antibodies were expressed and purified and tested in the ADAb inhibition assay, and in TNF-α binding affinity assays. The results for ADAb binding were averaged over 2 donors. Binding was assessed using surface plasmon resonance testing (Biacore). The results are shown in FIG. 22. The variants Y32K/SS-R30T and Y32K/SS-R30I exhibited the best combination of reduction in ADA binding and retained anti-TNF alpha affinity.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the disclosure(s).

What is claimed is:

1. A variant of a reference anti-TNF-α antibody or a reference anti-TNF-α binding fragment of an antibody, which reference antibody or binding fragment comprises six complementarity determining regions ("CDRs") having amino acid sequences corresponding to SEQ ID NO:5 (CDR-H1), SEQ ID NO:6 (CDR-H2), SEQ ID NO:7 (CDR-H3), SEQ ID NO:8 (CDR-L1), SEQ ID NO:9 (CDR-L2) and SEQ ID NO:10 (CDR-H3), wherein the variant comprises Y2K in CDR-H1,
  wherein the six CDRs altogether have up to 8 amino acid substitutions as compared to CDR sequences of the reference antibody or binding fragment.

2. The variant of claim 1, wherein the variant further includes the substitution R7I in CDR-L1 or R7T in CDR-L1.

3. A pharmaceutical composition comprising the anti-TNF-α antibody or anti-TNF-α binding fragment of claim 1 and a pharmaceutically acceptable carrier.

4. A method of treating a human patient suffering from an immune disorder comprising administering to the human patient a therapeutically effective amount of the anti-TNF-α antibody or anti-TNF-α binding fragment of claim 1.

5. The method of claim 4, wherein the immune disorder is selected from rheumatoid arthritis, juvenile idiopathic arthritis, psoriatic arthritis, ankylosing spondylitis, Crohn's disease, plaque psoriasis and axial spondyloarthritis.

6. The variant of claim 1, wherein the variant further includes the substitution T6V in CDR-H3.

7. The variant of claim 1, wherein the variant further includes the substitutions V1G in CDR-H3 and T6V in CDR-H3.

8. The variant of claim 1, wherein the variant further includes the substitutions G5S in CDR-L1 and A11S in CDR-L1.

9. The variant of claim 1, wherein the variant further includes the substitution R7I in CDR-L 1.

10. The variant of claim 1, wherein the variant further includes the substitutions G5S in CDR-L5, R7T in CDR-L1 and A11S in CDR-L1.

11. The variant of claim 1, wherein the variant further includes the substitutions G5S in CDR-L1, R7I in CDR-L1 and A11S in CDR-L1.

12. The variant of claim 1, wherein the reference anti-TNF-α antibody or reference anti-TNF-α binding fragment comprises a variable heavy chain fragment having an amino acid sequence corresponding to SEQ ID NO:2 and a variable light chain fragment having an amino acid sequence corresponding to SEQ ID NO:4.

* * * * *

UNITED STATES PATENT AND TRADEMARK OFFICE
CERTIFICATE OF CORRECTION

PATENT NO. : 9,279,016 B2  
APPLICATION NO. : 14/030977  
DATED : March 8, 2016  
INVENTOR(S) : Fiona A. Harding and Olivia Jennifer Razo Page 1 of 1

It is certified that error appears in the above-identified patent and that said Letters Patent is hereby corrected as shown below:

In the Specification:

Column 2, line 44, "SEQ ID NO:10 (CDR-H3)" should read "SEQ ID NO:10 (CDR-L3)"

In the Claims:

Column 37, line 16, claim 1, "ID NO:10 (CDR-H3)" should read "ID NO:10 (CDR-L3)"

Signed and Sealed this
Seventeenth Day of May, 2016

Michelle K. Lee
*Director of the United States Patent and Trademark Office*

SEQUENCE LISTING

```
<160> NUMBER OF SEQ ID NOS: 16

<210> SEQ ID NO 1
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaggtgcagc tggtggagtc tgggggaggc ttggtacagc ccggcaggtc cctgagactc      60
tcctgtgcgg cctctggatt cacctttgat gattatgcca tgcactgggt ccggcaagct     120
ccagggaagg gcctggaatg ggtctcagct atcacttgga atagtggtca catagactat     180
gcggactctg tggagggccg attcaccatc tccagagaca acgccaagaa ctccctgtat     240
ctgcaaatga acagtctgag agctgaggat acggccgtat attactgtgc gaaagtctcg     300
taccttagca ccgcgtcctc ccttgactat tggggccaag gtaccctggt caccgtctcg     360
agt                                                                   363

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30
```

```
Ala Met His Trp Val Arg Gln Ala Pro Gly Lys Gly Leu Glu Trp Val
         35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
             100                 105                 110

Gln Gly Thr Leu Val Thr Val Ser Ser
         115                 120
```

<210> SEQ ID NO 3
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
gacatccaga tgacccagtc tccatcctcc ctgtctgcat ctgtagggga cagagtcacc      60
atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa a                                               321
```

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Asp Ile Gln Met Thr Gln Ser Pro Ser Ser Leu Ser Ala Ser Val Gly
1                5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys
             100                 105
```

<210> SEQ ID NO 5
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 5

Asp Tyr Ala Met His
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ile Thr Trp Asn Ser Gly His Ile Asp Tyr Ala Asp Ser Val Glu
1               5                   10                  15
Gly

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Ser Tyr Leu Ser Thr Ala Ser Ser Leu Asp Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Ser Gln Gly Ile Arg Asn Tyr Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Ser Thr Leu Gln Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 10

Gln Arg Tyr Asn Arg Ala Pro Tyr Thr
1               5

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcgaaaata ataaagggaa aatcag                                          26

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tggtagtgtg gggactc                                                    17

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttagttgtgc tgcatcaggt tt                                              22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggtcaccagt gttccctgac                                                 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtaggcgaca gggtcacaat                                                 20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 16
agtccgtttg atctcgacct t                                        21
```